US009188589B2

(12) United States Patent
Schmidt et al.

(10) Patent No.: US 9,188,589 B2
(45) Date of Patent: *Nov. 17, 2015

(54) METHOD OF REVERSIBLY STAINING A TARGET CELL

(71) Applicant: IBA GMBH, Goettingen (DE)

(72) Inventors: Thomas Schmidt, Adelebsen (DE); Christian Stemberger, Holzkirchen (DE); Dirk H. Busch, Munich (DE); Lothar Germeroth, Goettingen (DE)

(73) Assignee: IBA GMBH, Goettingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/696,284

(22) Filed: Apr. 24, 2015

(65) Prior Publication Data

US 2015/0301046 A1    Oct. 22, 2015

Related U.S. Application Data

(63) Continuation of application No. 14/234,463, filed as application No. PCT/EP2012/063969 on Jul. 17, 2012, now Pat. No. 9,023,604.

(60) Provisional application No. 61/508,943, filed on Jul. 18, 2011.

(51) Int. Cl.
*G01N 31/00* (2006.01)
*G01N 33/53* (2006.01)
*G01N 33/569* (2006.01)
*A61K 35/14* (2015.01)
*A61K 35/17* (2015.01)

(52) U.S. Cl.
CPC .......... *G01N 33/56972* (2013.01); *A61K 35/14* (2013.01); *A61K 35/17* (2013.01); *G01N 2458/00* (2013.01)

(58) Field of Classification Search
CPC ........... C07K 2319/00; C07K 2319/22; C07K 2319/74; G01N 1/30; G01N 2333/705
See application file for complete search history.

(56) References Cited

U.S. PATENT DOCUMENTS

| 4,851,341 | A | 7/1989 | Hopp et al. |
| 5,506,121 | A | 4/1996 | Skerra et al. |
| 5,985,658 | A | 11/1999 | Colinas et al. |
| 7,482,000 | B2 | 1/2009 | Devaux et al. |
| 7,776,562 | B2 | 8/2010 | Busch et al. |
| 8,298,782 | B2 | 10/2012 | Busch et al. |
| 9,023,604 | B2 * | 5/2015 | Schmidt et al. ............. 435/7.21 |
| 2011/0070605 | A1 | 3/2011 | Busch et al. |

FOREIGN PATENT DOCUMENTS

| WO | 0254065 A2 | 7/2002 |
| WO | 02077018 A1 | 10/2002 |
| WO | 2010017103 A2 | 2/2010 |

OTHER PUBLICATIONS

Bes et al., Mapping the Paratope of Anti-CD4 Recombinant Fab 13B8.2 by Combining Parallel Peptide Synthesis and Site-directed Mutagenesis. J Biol Chem. Apr. 18, 2003;278(16):14265-14273.
Hoffmann et al., Only the CD45RA + subpopulation of CD4+CD25high T cells gives rise to homogeneous regulatory T-cell lines upon in vitro expansion. Blood. Dec. 15, 2006;108(13):4260-4267.
Huang et al., Facile Synthesis of Multivalent Nitrilotriacetic Acid (NTA) and NTA Conjugates for Analytical and Drug Delivery Applications. Bioconjug Chem. Nov.-Dec. 2006;17(6):1592-1600.
Ill et al., Design and construction of a hybrid immunoglobulin domain with properties of both heavy and light chain variable regions. Protein Eng. Aug. 1997;10(8):949-957.
Kolb et al., Donor leukocyte transfusions for treatment of recurrent chronic myelogenous leukemia in marrow transplant patients. Blood. Dec. 15, 1990;76(12):2462-2465.
Kwong et al., Generation, affinity maturation, and characterization of a human anti-human NKG2D monoclonal antibody with dual antagonistic and agonistic activity. J Mol Biol. Dec. 31, 2008;384(5):1143-1156.
Lata et al., High-Affinity Adaptors for Switchable Recognition of Histidine-Tagged Proteins. J Am Chem Soc. Jul. 27, 2005;127(29)10205-10215.
Martin et al., The affinity-selection of a minibody polypeptide inhibitor of human interleukin-6. EMBO J. Nov. 15, 1994;13(22):5303-5309.
Miyara et al., Functional Delineation and Differentiation Dynamics of Human CD4+ T Cells Expressing the FoxP3 Transcription Factor. Immunity. Jun. 19, 2009;30(6):899-911.
Noguchi et al., Preparation and Properties of the Immunoconjugate Composed of Anti-Human Colon Cancer Monoclonal Antibody and Mitomycin C-Dextran Conjugate. Bioconjug Chem. Mar.-Apr. 1992;3(2):132-137.
Pluckthun and Skerra, Expression of Functional Antibody Fv and Fab Fragments in *Escherichia coli*. Methods Enzymol. 1989;178:497-515.
Randolph and Fathman, CD4+CD25+ Regulatory T Cells and Their Therapeutic Potential. Annu Rev Med. 2006;57:381-402.
Riddell et al., Restoration of Viral Immunity in Immunodeficient Humans by the Adoptive Transfer of T Cell Clones. Science. Jul. 10, 1992;257(5067):238-241.

(Continued)

*Primary Examiner* — Lisa Cook
(74) *Attorney, Agent, or Firm* — Michael A. Whittaker

(57) ABSTRACT

The present invention relates to methods of treating a subject with a population of target cells defined by the presence of a specific receptor molecule on the surface; wherein the population of target cells is isolated by a method of reversibly staining the target cells with a detectable label.

20 Claims, 4 Drawing Sheets

(56) References Cited

OTHER PUBLICATIONS

Riley et al., Human T Regulatory Cell Therapy: Take a Billion or So and Call Me in the Morning. Immunity. May 2009;30(5):656-665.

Rooney et al., Use of gene-modified virus-specific T lymphocytes to control Epstein-Barr-virus-related lymphoproliferation. Lancet. Jan. 7, 1995;345(8941):9-13.

Schlapschy et al., Functional humanization of an anti-CD30 Fab fragment for the immunotherapy of Hodgkin's lymphoma using an in vitro evolution approach. Protein Eng Des Sel. Dec. 2004;17(12):847-860.

Schmidt and Skerra, The Strep-tag system for one-step purification and high-affinity detection or capturing of proteins. Nat Protoc. 2007;2(6):1528-1535.

Silverman et al., Multivalent avimer proteins evolved by exon shuffling of a family of human receptor domains. Nat Biotechnol. Dec. 2005;23(12):1556-1561.

Traunecker et al., Bispecific single chain molecules (Janusins) target cytotoxic lymphocytes on HIV infected cells. EMBO J. Dec. 1991;10(12):3655-3659.

International Search Report and Written Opinion issued in PCT/EP20121063969 dated Mar. 12, 2013.

Bouquie et al., A fast and efficient HLA multimer-based sorting procedure that induces little apoptosis to isolate clinical grade human tumor specific T lymphocytes. Cancer Immunol Immunother. Apr. 2009;58(4):553-566.

Casalegno-Garduño et al., Multimer technologies for detection and adoptive transfer of antigen-specific T cells. Cancer Immunol Immunother. Feb. 2010;59(2):195-202.

Knabel et al., Reversible MHC multimer staining for functional isolation of T-cell populations and effective adoptive transfer. Nat Med. Jun. 2002;8(6): 631-637.

Matsui et al., Kinetics Oft-Cell Receptor Binding to Peptide/I-Ek Complexes Correlation of the Dissociation Rate with T-Cell Responsiveness. Proc Natl Acad Sci U S A. Dec. 20, 1994;91(26):12862-12866.

Neudorfer et al., Reversible HLA multimers (Streptamers) for the isolation of human cytotoxic T lymphocytes functionally active against tumor- and virus-derived antigens. J Immunol Methods. Mar. 30, 2007;320(1-2):119-131.

Odendahl et al., GMP Compliant Isolation of Untouched Cmv-Specific Donor Derived CD3+CD8+T Lymphocytes Using Streptamer-Technology. Vox Sanguinis, Jun. 2010;99(Suppl.I):490-491.

Schmitt et al., Adoptive transfer and selective reconstitution of streptamer-selected cytomegalovirus-specific CD8+ T cells leads to virus clearance in patients after allogeneic peripheral blood stem cell transplantation. Transfusion. Mar. 2011;51(3):591-599.

Schroeder, Nach Zellen Angeln. Faszination Forschung Jun. 30, 2010:28-37 Retrieved from the Internet: URL:http://portal.mytum.de/pressestelle/faszination-forschung/2010nr6/index html [retrieved on Nov. 16, 2012]—p. 34-p. 37.

Stemberger et al., Novel Serial Positive Enrichment Technology Enables Clinical Multiparameter Cell Sorting. PLoS One. 2012;7(4):e35798 (11 pp).

Office Action issued by SIPO in PRC application No. 201280045377.8 dated May 28, 2015—incl Engl lang transl.

* cited by examiner

SEQUENCE LISTING

<160> NUMBER OF SEQ ID NOS: 16

<210> SEQ ID NO 1
<211> LENGTH: 8
<212> TYPE: PRT
<213> ORGANISM: Artificial Sequence
<220> FEATURE:
<223> OTHER INFORMATION: streptavidin-binding peptide

<400> SEQUENCE: 1

```
Trp Ser His Pro Gln Phe Glu Lys
1               5

<210> SEQ ID NO 2
<211> LENGTH: 4
<212> TYPE: PRT
<213> ORGANISM: Artificial Sequence
<220> FEATURE:
<223> OTHER INFORMATION: streptavidin analog (amino acid position 44-47)

<400> SEQUENCE: 2

Val Thr Ala Arg
1

<210> SEQ ID NO 3
<211> LENGTH: 4
<212> TYPE: PRT
<213> ORGANISM: Artificial Sequence
<220> FEATURE:
<223> OTHER INFORMATION: streptavidin analog (amino acid position 44-47)

<400> SEQUENCE: 3

Ile Gly Ala Arg
1

<210> SEQ ID NO 4
<211> LENGTH: 10
<212> TYPE: PRT
<213> ORGANISM: Artificial Sequence
<220> FEATURE:
<223> OTHER INFORMATION: Myc-tag

<400> SEQUENCE: 4

Glu Gln Lys Leu Ile Ser Glu Glu Asp Leu
1               5                   10

<210> SEQ ID NO 5
<211> LENGTH: 9
<212> TYPE: PRT
<213> ORGANISM: Artificial Sequence
<220> FEATURE:
<223> OTHER INFORMATION: HA-tag

<400> SEQUENCE: 5

Tyr Pro Tyr Asp Val Pro Asp Tyr Ala
1               5

<210> SEQ ID NO 6
<211> LENGTH: 11
<212> TYPE: PRT
<213> ORGANISM: Artificial Sequence
<220> FEATURE:
<223> OTHER INFORMATION: VSV-G-tag

<400> SEQUENCE: 6

Tyr Thr Asp Ile Glu Met Asn Arg Leu Gly Lys
1               5                   10

<210> SEQ ID NO 7
<211> LENGTH: 11
<212> TYPE: PRT
<213> ORGANISM: Artificial Sequence
<220> FEATURE:
<223> OTHER INFORMATION: HSV-tag

<400> SEQUENCE: 7

Gln Pro Glu Leu Ala Pro Glu Asp Pro Glu Asp
```

-continued

```
1               5                   10
```

<210> SEQ ID NO 8
<211> LENGTH: 14
<212> TYPE: PRT
<213> ORGANISM: Artificial Sequence
<220> FEATURE:
<223> OTHER INFORMATION: V5-tag

<400> SEQUENCE: 8

```
Gly Lys Pro Ile Pro Asn Pro Leu Leu Gly Leu Asp Ser Thr
1               5                   10
```

<210> SEQ ID NO 9
<211> LENGTH: 8
<212> TYPE: PRT
<213> ORGANISM: Artificial Sequence
<220> FEATURE:
<223> OTHER INFORMATION: FLAG-tag

<400> SEQUENCE: 9

```
Asp Tyr Lys Asp Asp Asp Asp Lys
1               5
```

<210> SEQ ID NO 10
<211> LENGTH: 30
<212> TYPE: PRT
<213> ORGANISM: Artificial Sequence
<220> FEATURE:
<223> OTHER INFORMATION: sequential arrangement of two streptavidin
      binding modules

<400> SEQUENCE: 10

```
Ser Ala Trp Ser His Pro Gln Phe Glu Lys Gly Gly Gly Ser Gly Gly
1               5                   10                  15

Gly Ser Gly Gly Ser Ala Trp Ser His Pro Gln Phe Glu Lys
            20                  25                  30
```

<210> SEQ ID NO 11
<211> LENGTH: 253
<212> TYPE: PRT
<213> ORGANISM: human
<220> FEATURE:
<223> OTHER INFORMATION: Heavy Chain of Fab Fragment 13B8.2

<400> SEQUENCE: 11

```
Ala Met Gln Val Gln Leu Lys Gln Ser Gly Pro Gly Leu Val Gln Pro
1               5                   10                  15

Ser Gln Ser Leu Ser Ile Thr Cys Thr Val Ser Gly Phe Ser Leu Thr
            20                  25                  30

Thr Phe Gly Val His Trp Val Arg Gln Ser Pro Gly Lys Gly Leu Glu
        35                  40                  45

Trp Leu Gly Val Ile Trp Arg Ser Gly Ile Thr Asp Tyr Asn Val Pro
    50                  55                  60

Phe Met Ser Arg Leu Ser Ile Thr Lys Asp Asn Ser Lys Ser Gln Val
65                  70                  75                  80

Phe Phe Lys Leu Asn Ser Leu Gln Pro Asp Asp Thr Ala Ile Tyr Tyr
                85                  90                  95

Cys Ala Lys Asn Asp Pro Gly Thr Gly Phe Ala Tyr Trp Gly Gln Gly
            100                 105                 110

Thr Leu Val Thr Val Ser Ala Gly Ser Thr Lys Gly Pro Ser Val Phe
        115                 120                 125
```

```
Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Gly Ser
    210                 215                 220

Ala Trp Ser His Pro Gln Phe Glu Lys Gly Gly Ser Gly Gly Gly
225                 230                 235                 240

Ser Gly Gly Ser Ala Trp Ser His Pro Gln Phe Glu Lys
                245                 250
```

<210> SEQ ID NO 12
<211> LENGTH: 218
<212> TYPE: PRT
<213> ORGANISM: human
<220> FEATURE:
<223> OTHER INFORMATION: Light Chain of Fab Fragment 13B8.2

<400> SEQUENCE: 12

```
Ala Met Asp Ile Gln Met Thr Gln Ser Pro Ala Ser Leu Ser Ala Ser
1               5                   10                  15

Val Gly Glu Thr Val Thr Phe Thr Cys Arg Ala Ser Glu Met Ile Tyr
            20                  25                  30

Ser Tyr Leu Ala Trp Tyr Gln Gln Lys Gln Gly Lys Ser Pro Gln Leu
        35                  40                  45

Leu Val His Asp Ala Lys Thr Leu Ala Glu Gly Val Pro Ser Arg Phe
    50                  55                  60

Ser Gly Gly Gly Ser Gly Thr Gln Phe Ser Leu Lys Ile Asn Thr Leu
65                  70                  75                  80

Gln Pro Glu Asp Phe Gly Thr Tyr Tyr Cys Gln His Tyr Gly Asn
                85                  90                  95

Pro Pro Thr Phe Gly Gly Gly Thr Lys Leu Glu Ile Lys Arg Gly Ile
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys Gly Ser
    210                 215
```

<210> SEQ ID NO 13
<211> LENGTH: 253

<212> TYPE: PRT
<213> ORGANISM: human
<220> FEATURE:
<223> OTHER INFORMATION: Heavy Chain of Fab Fragment Mutant M1

<400> SEQUENCE: 13

Ala Met Gln Val Gln Leu Lys Gln Ser Gly Pro Gly Leu Val Gln Pro
1               5                   10                  15

Ser Gln Ser Leu Ser Ile Thr Cys Thr Val Ser Gly Phe Ser Leu Thr
            20                  25                  30

Thr Phe Gly Val His Trp Val Arg Gln Ser Pro Gly Lys Gly Leu Glu
        35                  40                  45

Trp Leu Gly Val Ile Trp Arg Ser Gly Ile Thr Asp Tyr Asn Val Pro
    50                  55                  60

Phe Met Ser Arg Leu Ser Ile Thr Lys Asp Asn Ser Lys Ser Gln Val
65                  70                  75                  80

Phe Phe Lys Leu Asn Ser Leu Gln Pro Asp Asp Thr Ala Ile Tyr Tyr
                85                  90                  95

Cys Ala Lys Asn Asp Pro Gly Thr Gly Ala Ala Tyr Trp Gly Gln Gly
            100                 105                 110

Thr Leu Val Thr Val Ser Ala Gly Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Gly Ser
    210                 215                 220

Ala Trp Ser His Pro Gln Phe Glu Lys Gly Gly Gly Ser Gly Gly Gly
225                 230                 235                 240

Ser Gly Gly Ser Ala Trp Ser His Pro Gln Phe Glu Lys
                245                 250

<210> SEQ ID NO 14
<211> LENGTH: 218
<212> TYPE: PRT
<213> ORGANISM: human
<220> FEATURE:
<223> OTHER INFORMATION: Light Chain of Fab Fragment Mutant M2

<400> SEQUENCE: 14

Ala Met Asp Ile Gln Met Thr Gln Ser Pro Ala Ser Leu Ser Ala Ser
1               5                   10                  15

Val Gly Glu Thr Val Thr Phe Thr Cys Arg Ala Ser Glu Met Ile Tyr
            20                  25                  30

Ser Tyr Leu Ala Trp Tyr Gln Gln Lys Gln Gly Lys Ser Pro Gln Leu
        35                  40                  45

Leu Val His Asp Ala Lys Thr Leu Ala Glu Gly Val Pro Ser Arg Phe
    50                  55                  60

Ser Gly Gly Gly Ser Gly Thr Gln Phe Ser Leu Lys Ile Asn Thr Leu
65                  70                  75                  80

```
Gln Pro Glu Asp Phe Gly Thr Tyr Tyr Cys Gln His His Ala Gly Asn
                85                  90                  95

Pro Pro Thr Phe Gly Gly Gly Thr Lys Leu Glu Ile Lys Arg Gly Ile
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys Gly Ser
        210                 215

<210> SEQ ID NO 15
<211> LENGTH: 253
<212> TYPE: PRT
<213> ORGANISM: human
<220> FEATURE:
<223> OTHER INFORMATION: Heavy Chain of Fab Fragment Mutant M3

<400> SEQUENCE: 15

Ala Met Gln Val Gln Leu Lys Gln Ser Gly Pro Gly Leu Val Gln Pro
1               5                   10                  15

Ser Gln Ser Leu Ser Ile Thr Cys Thr Val Ser Gly Phe Ser Leu Thr
            20                  25                  30

Thr Phe Gly Val Ala Trp Val Arg Gln Ser Pro Gly Lys Gly Leu Glu
        35                  40                  45

Trp Leu Gly Val Ile Trp Arg Ser Gly Ile Thr Asp Tyr Asn Val Pro
    50                  55                  60

Phe Met Ser Arg Leu Ser Ile Thr Lys Asp Asn Ser Lys Ser Gln Val
65                  70                  75                  80

Phe Phe Lys Leu Asn Ser Leu Gln Pro Asp Asp Thr Ala Ile Tyr Tyr
                85                  90                  95

Cys Ala Lys Asn Asp Pro Gly Thr Gly Phe Ala Tyr Trp Gly Gln Gly
            100                 105                 110

Thr Leu Val Thr Val Ser Ala Gly Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Gly Ser
    210                 215                 220
```

```
Ala Trp Ser His Pro Gln Phe Glu Lys Gly Gly Gly Ser Gly Gly Gly
225                 230                 235                 240

Ser Gly Gly Ser Ala Trp Ser His Pro Gln Phe Glu Lys
                245                 250

<210> SEQ ID NO 16
<211> LENGTH: 218
<212> TYPE: PRT
<213> ORGANISM: human
<220> FEATURE:
<223> OTHER INFORMATION: Light Chain of Fab Fragment Mutant M4

<400> SEQUENCE: 16

Ala Met Asp Ile Gln Met Thr Gln Ser Pro Ala Ser Leu Ser Ala Ser
1               5                   10                  15

Val Gly Glu Thr Val Thr Phe Thr Cys Arg Ala Ser Glu Met Ile Tyr
            20                  25                  30

Ser Tyr Leu Ala Trp Tyr Gln Gln Lys Gln Gly Lys Ser Pro Gln Leu
        35                  40                  45

Leu Val His Asp Ala Lys Thr Leu Ala Glu Gly Val Pro Ser Arg Phe
    50                  55                  60

Ser Gly Gly Ser Gly Thr Gln Phe Ser Leu Lys Ile Asn Thr Leu
65                  70                  75                  80

Gln Pro Glu Asp Phe Gly Thr Tyr Tyr Cys Gln His Ala Tyr Gly Asn
                85                  90                  95

Pro Pro Thr Phe Gly Gly Gly Thr Lys Leu Glu Ile Lys Arg Gly Ile
            100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
        130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys Gly Ser
        210                 215
```

METHOD OF REVERSIBLY STAINING A TARGET CELL

CROSS-REFERENCE TO RELATED APPLICATIONS

This application is a continuation of application Ser. No. 14/234,463, filed Apr. 18, 2014, now U.S. Pat. No. 9,023,604, issued May 5, 2015, which is the National Stage of International Application No. PCT/EP2012/063969, filed Jul. 17, 2012, which claims the benefit of U.S. Provisional Application No. 61/508,943, filed Jul. 18, 2011, the contents of each of which are hereby incorporated by reference in their entirety for all purposes.

SEQUENCE LISTING

The instant application contains a Sequence Listing which has been submitted in ASCII format via EFS-Web and is hereby incorporated by reference in its entirety. Said ASCII copy, created on Apr. 24, 2015, is named SCH2900CT_SeqListing.txt and is 15 kilobytes in size.

FIELD OF THE INVENTION

The present invention relates to methods of reversibly staining a target cell. The invention also relates to methods of isolating a target cell or a target cell population that is defined by the presence of at least one common specific receptor molecule. The invention also provides kits that can be used to carry out the methods of the invention.

BACKGROUND OF THE INVENTION

Cell therapy has proven to be highly effective for the treatment of a number of diseases. For example, primary immunodeficiencies can be cured by hematopoetic stem cell transplantation (HSCT) and some leukemia can be brought to complete remission by combined allogeneic HSCT and donor lymphocyte infusion (DLI) (Kolb, H. J. et al., Donor leukocyte transfusions for treatment of recurrent chronic myelogenous leukemia in marrow transplant patients. *Blood* 76 (12), 2462-2465 (1990). In some clinical settings, adoptive transfer of virus-specific T cells is very effective to reconstitute immunocompromised patients against life-threatening complications caused by cytomegalovirus (CMV) reactivation (Riddell, S. R. et al., Restoration of viral immunity in immunodeficient humans by the adoptive transfer of T cell clones. *Science* 257 (5067), 238-241 (1992)), or lymphoproliferative diseases mediated by Epstein-Ban-Virus (EBV) (Rooney, C. M. et al., Use of gene-modified virus-specific T lymphocytes to control Epstein-Ban-virus-related lymphoproliferation. *Lancet* 345 (8941), 9-13 (1995)). Similarly, tumor antigen-directed T cells, either derived from autologous tumor-infiltrating lymphocytes or cultured or engineered in vitro, are promising candidates for improved therapies.

Regardless of these interesting clinical observations, a broader transfer of cell therapy to clinical applications is still awaiting. This is mainly due to the fact that most procedures used to generate cell preparations for immunotherapy are very laborious, time consuming and expensive. Furthermore, cell populations known to mediate clinical effects usually need to be enriched to high purities, since contaminating 'unwanted' cells can mediate harmful and sometimes life-threatening side effects (like graft-versus-host-diseases (GvHD)-mediating alloreactive T cells upon allogeneic stem cell transplantation and/or DLI treatment). As it has been shown that already very low numbers of adoptively transferred T cells can contribute to beneficial clinical effects, similar rules will also apply for cell populations mediating negative side effects. Therefore, providing high purities of well-defined cell preparations applicable for therapy will become key to make these promising therapies more effective and predictable, as well as to lower the risk of potential side effects.

Current methods for surface marker-mediated clinical cell purification usually rely on single parameters (e.g. CD34, MHC multimers). However, for most cell populations—either directly derived ex vivo or after in vitro cell culture—a combination of different surface markers is necessary in order to truly segregate these cells from others. For example, naturally occurring regulatory T cells (Tregs) represent a promising cell subset, which might be able to prevent acute GvHD upon allogeneic HSCT 4 or the development of autoimmune diseases (Riley, J. L., June, C. H., & Blazar, B. R., Human T regulatory cell therapy: take a billion or so and call me in the morning. *Immunity* 30 (5), 656-665 (2009), Randolph, D. A. & Fathman, C. G., Cd4+Cd25+ regulatory T cells and their therapeutic potential. *Annu Rev Med* 57, 381-402 (2006)).

Beside the expression of CD4, which is shared by a large number of cells, additional markers like their constitutive expression of the high-affinity IL-2 receptor a-chain (CD25) are needed to further narrow down heterogeneity. However, CD25 is also expressed on a large fraction of non-regulatory cells, which include recently activated effector and memory T cells. Therefore, combinatorial staining patterns, like combinations of CD4, CD25, CD127, and CD45RA (Miyara, M. et al., Functional delineation and differentiation dynamics of human CD4+ T cells expressing the FoxP3 transcription factor. *Immunity* 30 (6), 899-911 (2009), Hoffmann, P. et al., Only the CD45RA+ subpopulation of CD4+CD25high T cells gives rise to homogeneous regulatory T-cell lines upon in vitro expansion. *Blood* 108 (13), 4260-4267 (2006)) have been suggested to more precisely identify this clinically relevant T cell subset.

All currently available clinical marker-based cell separation techniques utilize paramagnetic beads, which retain labeled cell populations within a magnetic field. Thereby, positive enrichment strategies using directly labeled target populations give highest purities. However, combinations of purifications via several different markers are still difficult to achieve, although being necessary to isolate distinct cell populations of highest purity. In addition, after positive selection, both labels and beads usually remain on the cell product, potentially manipulating the isolated cell population or negatively impacting its functionality/viability e.g. by receptor blockade. Especially in respect to clinical cell sorting, remaining cell labels cause substantial regulatory hurdles for the applicability of cell products into patients. In order to circumvent the problems of positive selection, many clinical cell processing procedures have been changed to depletion settings. Unfortunately, target cell purities are often poor and depletion methods often require a complicated cocktail of different antibodies, which makes their production and application laborsome and expensive.

Thus, there is still a need to provide a method for cell purification or isolation that allows, for example after cell sorting, the release and complete removal of all components of the receptor binding and staining reagents from the purified cell population.

SUMMARY OF INVENTION

In one aspect the invention provides a method of reversibly staining a target cell, said target cell comprising a receptor molecule on the surface thereof, with a detectable label, the method comprising:
contacting a mixture of cells comprising said target cell with
(i) a receptor binding reagent, the receptor binding reagent comprising at least one (any) binding site B, wherein the binding site B specifically binds to said receptor molecule, wherein the dissociation rate constant ($k_{off}$) for the binding between said receptor binding reagent via the binding site B and said receptor molecule has a value of about $0.5 \times 10^{-4}$ $\sec^{-1}$ or greater, the receptor binding reagent further comprising at least one binding partner C, wherein the binding partner C is able of being (reversibly) bound to a binding site Z of a multimerization reagent,
(ii) a multimerization reagent, the multimerization reagent comprising at least two binding sites Z for the reversible binding of the binding partner C of the receptor binding reagent, wherein the receptor binding reagent (i) and the multimerization reagent (ii) form (a plurality of) multivalent binding complexes that bind to said target cell, each multivalent binding complex comprising at least two of said receptor binding reagents bound to one said multimerization reagent, said multivalent binding complex providing increased avidity, relative to said receptor binding reagent; and
(iii) said detectable label bound to said multivalent binding complex,
wherein said target cell is stained by binding of said multivalent binding complex to said target cell, and wherein staining of said target cell is reversible upon disruption of the binding between said binding partner C of said receptor binding reagent and said binding sites Z of said multimerization reagent.

In a second aspect, the invention provides the use of such staining method for the isolation of a target cell population that is defined by the presence of a (at least one common specific) receptor molecule.

In a further aspect the invention provides a kit for reversibly staining a target cell (or isolating a target cell), said target cell comprising a receptor molecule on its surface, with a detectable label. Such a kit comprises:
(i) at least one receptor binding reagent comprising a (any) binding site B which specifically binds to said receptor molecule, wherein the dissociation rate constant ($k_{off}$) for the binding between said receptor binding reagent via the binding site B and said receptor binding molecule has a value of about $0.5 \times 10^{-4}$ $\sec^{-1}$ or greater, and the receptor binding reagent further comprising at least one binding partner C, wherein the binding partner C is able of being (reversibly) bound by a binding site Z of a multimerization agent,
(ii) at least one multimerization reagent comprising at least two binding sites Z for said binding partner C of the receptor binding reagent, wherein the binding partner C and said binding sites Z of said multimerization reagent are capable of forming a reversible bond,
(iii) a detectable label bound or capable of binding to the receptor binding reagent (i) and/or the multimerization reagent (ii).

In a further aspect, the invention provides the use of a receptor binding reagent which specifically binds to a receptor molecule, the receptor binding reagent comprising at least one binding site B, wherein the binding site B specifically binds to said receptor molecule, wherein the dissociation rate constant ($k_{off}$) for the binding between said receptor binding reagent via the binding site B and said receptor molecule has a value of about $0.5 \times 10^{-4}$ $\sec^{-1}$ or greater, for a method of reversibly staining a target cell.

In yet a further aspect, the invention provides a method of reversibly staining a target cell, said target cell comprising a (at least one) receptor molecule on the surface thereof, with a detectable label, the method comprising:
contacting a mixture of cells comprising said target cell with
(i) at least two kinds of a receptor binding reagent, each kind of the receptor binding reagent comprising at least one binding site B, wherein the binding site B of each of the kind of receptor binding reagent specifically binds to said receptor molecule, wherein the dissociation rate constant ($k_{off}$) for the binding between each kind of said receptor binding reagent via the binding site B and said receptor molecule has a value of about $0.5 \times 10^{-4}$ $\sec^{-1}$ or greater, each kind of the receptor binding reagent further comprising at least one binding partner C, wherein the binding partner C of each kind of receptor binding reagent is able of being reversibly bound to a binding site Z of a multimerization reagent,
(ii) a multimerization reagent, the multimerization reagent comprising at least one binding site Z for the reversibly binding of the binding partner C of each kind of the receptor binding reagent,
wherein the at least two kinds of receptor binding reagent (i) and the multimerization reagent (ii) form (a plurality of) multivalent binding complexes that bind to said target cell, each multivalent binding complex comprising at least one of each kind of receptor binding reagent bound to one said multimerization reagent, said multivalent binding complex providing increased avidity, relative to each kind of said receptor binding reagent; and
(iii) said detectable label bound to said multivalent binding complex,
wherein said target cell is stained by binding of said multivalent binding complex to said target cell, and wherein staining of said target cell is reversible upon disruption of the binding between said binding partner C of each kind of said receptor binding reagent and said binding sites Z of said multimerization reagent.

In yet another aspect, the invention provides a reagent kit for reversibly staining (or isolating) a target cell, said target cell comprising a receptor molecule on the surface thereof, with a detectable label, the kit comprising:
(i) at least two kinds of a receptor binding reagent comprising a binding site B which specifically binds to said receptor molecule, wherein the dissociation rate constant ($k_{off}$) for the binding between each kind of said receptor binding reagent via the binding site B and said receptor binding molecule has a value of about $0.5 \times 10^{-4}$ $\sec^{-1}$ or greater, and each kind of the receptor binding reagent further comprising at least one binding partner C, wherein the binding partner C of each kind of the receptor binding reagent is able of being (reversibly) bound by a binding site Z of a multimerization reagent,
(ii) at least one multimerization reagent comprising at least one binding site Z for said binding partner C of each kind of the receptor binding reagent, wherein the binding partner C of each kind of binding reagent and said binding sites Z of said multimerization reagent are capable of forming a reversible bond,
(iii) a detectable label bound or capable of binding to the receptor binding reagent (i) and/or the multimerization reagent (ii).

BRIEF DESCRIPTION OF THE DRAWINGS

The invention will be better understood with reference to the detailed description when considered in conjunction with the non-limiting examples and the accompanying drawings, in which:

FIG. 1a shows an illustrative example of a Fab fragment that is used as receptor binding reagent, in which a streptavidin binding peptide, the Strep-Tag® is the binding partner C of the receptor binding reagent. In this embodiment the streptavidin binding peptide is fused or conjugated to the Fab fragment to form the receptor binding reagent. In this example as shown in FIG. 1a, the multimerization reagent that comprises at least two binding sites Z for said at least one binding partner C is a streptavidin mutein ("Strep-Tactin®"). In the example of FIG. 1a the multimerization reagent carries a fluorescent label such as phycoerythrin. In the example of FIG. 1b again a Fab fragment is shown together with a multimerization reagent that is conjugated to a magnetic bead that serves as label. The reversible staining method using the multivalent binding complex formation between the streptavidin-mutein and a Fab fragment via the streptavidin-binding peptide is also herein referred to as "Fab-multimer staining". FIG. 1c depicts a schematic overview of this reversible Fab-multimer staining method. In this example, target cells are stained/isolated from a mixture of cells present in a blood sample. Fab-fragments with a $k_{off}$-rate of about $0.5 \times 10^{-1}$ sec$^{-1}$ or greater for the binding to a cell receptor molecule that is present on a target cell are reversibly multimerized by Strep-Tag®/Strep-Tactin® complex formation. Target cells are stained with the multivalent binding complex (by contacting the cells with the multimerization reagent and the receptor binding reagent as shown in step a) of FIG. 1c) and optionally separated from other cells that are devoid of the cognate cell surface receptor molecule, for example, by fluorescence-activated cell sorting (also known under the trademark "FACS™" in step b) of FIG. 1c). Subsequent treatment of isolated stained target cells with the Strep-Tactin® ligand D-biotin competing with the Strep-Tag® peptide causes displacement of the Fab fragments from the multimerization reagent, thereby releasing the multimerization reagent (Strep-Tactin® complex) from the target cell (as shown in step c) of FIG. 1c). Remaining Fab fragments, uncomplexed from Strep-Tactin®, (spontaneously) dissociate in a reasonable time window due to their high $k_{off}$-rate and can be completely removed from the target cell surface by washing (step d) of FIG. 1c). The washing can be carried out in a volume diluting the Fab fragments during each washing step to at least to a concentration equaling to the affinity dissociation constant ($K_d$) for the binding between the Fab fragment and the cognate cell surface receptor molecule. FIG. 1d shows the analogous staining procedure to that of FIG. 1c in which the multimerization reagent is conjugated to a magnetic bead and in which the staining/separation step includes separation of stained cells from unstained cells via a magnetic column on which the stained cells are bound.

FIG. 2 shows a FACS analysis of anti-CD4 Fab-multimer staining with different anti-CD4 Fab mutants with increasing $k_{off}$-rates for the binding of the Fab fragments to CD4 as a receptor molecule (a summary of the binding kinetics of the Fab fragments is listed in Table 1). Peripheral Blood Mononuclear Cells (PBMCs) were stained with anti-CD4 Fab fragments (receptor binding reagent) fused to a sequential arrangement of two Strep-Tag® sequences (commercially available under the trade name "One-STrEP-tag"; binding partner C) and multimerized on phycoerythrin labeled Strep-Tactin® (Strep-Tactin PE; IBA GmbH, Göttingen, Germany; multimerization reagent comprising at least 2 binding sites Z for the binding partner C) and analyzed either before (second column) or after treatment with D-biotin (third column). Remaining Fab-monomers (i.e. Fab fragments used as receptor binding reagent) on the target cell surface were then detected after subsequent washing steps to remove the Fab monomers using Strep-Tactin PE alone (without bound Fab fragments) (fourth column). Fab-multimer staining after the reversible staining described above of the cells was performed again (fifth column) to control completion of biotin removal which otherwise would have hampered the staining of remaining Fab-monomers with Strep-Tactin PE alone (without bound Fab fragments) as shown in the fourth column and which thus would have led to a wrong conclusion of the experiment. Alternatively, cells were incubated with monomeric Fab-fragments, washed and subsequently analyzed after staining with Strep-Tactin® PE (first, i.e. left-most column). Live CD3$^+$ T cells are shown. Numbers in the dot plots indicate the percentage of cells within gates.

DETAILED DESCRIPTION OF THE INVENTION

Figure 1A:
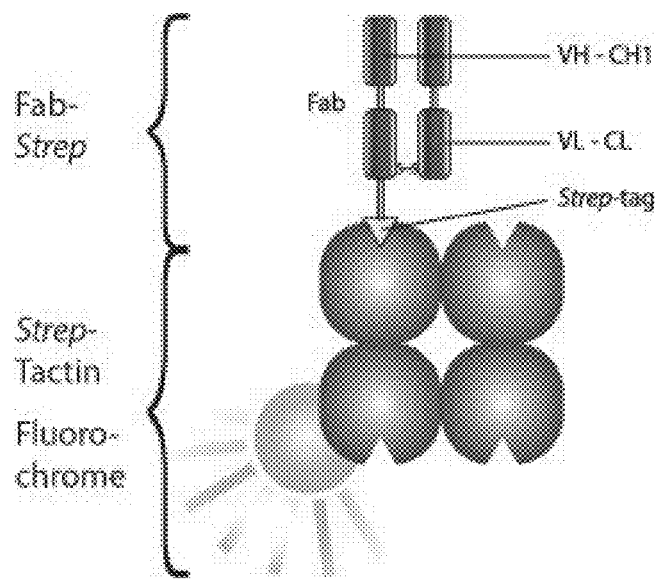
FIG. 1a to FIG. 1d depict the principle of the reversible staining method of the invention using a Fab fragment as a (at least one) receptor binding reagent (in the case of a Fab fragment and also generally in one embodiment of the invention, the receptor binding reagent can have a single binding site for the receptor molecule).
Figure 1B:
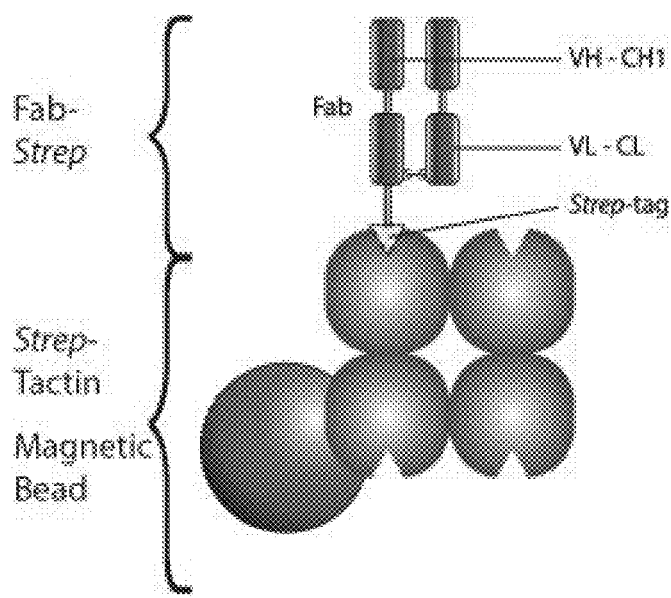
Figure 1C:
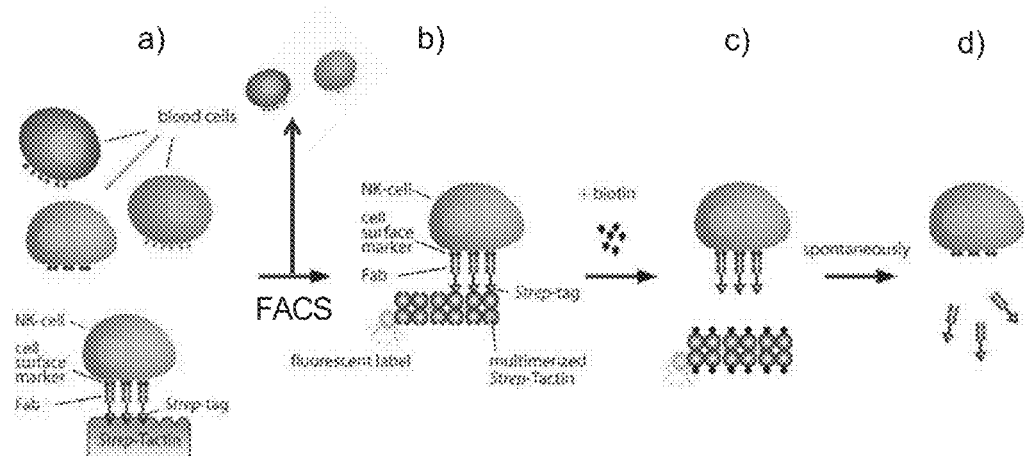
Figure 1D:
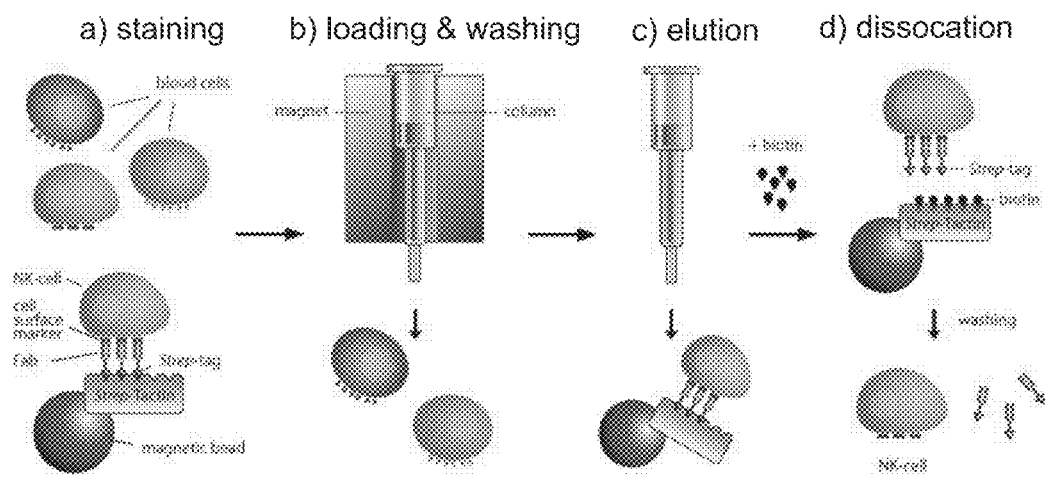

The present invention provides a method for reversibly staining a target cell or a target cell population having a receptor molecule on the cell surface. The invention is based on the finding that, in contrast to the methods described in U.S. Pat. No. 7,776,562 or International Patent application WO02/054065, it is not essential for the reversibility of such a method that a low affinity binding is given between a receptor binding reagent and a receptor molecule on the surface of the target cell. Rather it has been found in the current invention that irrespective of the strength of the binding, meaning whether the dissociation constant ($K_d$) for the binding between the receptor binding reagent and the receptor molecule is of low affinity, for example, in the range of a $K_d$ of about $10^{-3}$ to about $10^{-7}$ M, or of high affinity, for example, in the range of a $K_d$ of about $10^{-7}$ to about $1 \times 10^{-10}$ M, a target cell can be reversibly stained as long as the dissociation of the binding of the receptor binding reagent via the binding site B and the receptor molecule occurs sufficiently fast. Expressed in terms of the $k_{off}$-rate (also called dissociation rate constant for the binding between the receptor binding reagent (via the binding site B) and the receptor molecule, the $k_{off}$-rate is about $0.5 \times 10^{-4}$ sec$^{-1}$ or greater, about $1 \times 10^{-4}$ sec$^{-1}$ or greater, about $2 \times 10^{-4}$ sec$^{-1}$ or greater, about $3 \times 10^{-4}$ sec$^{-1}$ or greater, about $4 \times 10^{-4}$ sec$^{-1}$ of greater, about $5 \times 10^{-4}$ sec$^{-1}$ or greater, about 1×10⁻³ sec⁻¹ or greater, about 1.5×10⁻³ sec⁻¹ or greater, about 2×10⁻³ sec⁻¹ or greater, about 3×10⁻³ sec⁻¹ or greater, about 4×10⁻³ sec⁻¹, about 5×10⁻³ sec⁻¹ or greater, about 1×10⁻² sec⁻¹ or greater, or about 5×10⁻¹ sec⁻¹ or greater. The term "about" when used herein in relation to the $k_{off}$ rate, the $k_{on}$ rate or the $K_d$ is meant to include an error margin of ±0.1%, ±0.2%, ±0.3%, ±0.4%, ±0.5%, ±0.7±0.9, %±1.0, %, ±1.2%, ±1.4%±1.6%, ±1.8,%±2.0%, ±2.2%, ±2.4,%, ±2.6%, ±2.8%, ±3.0%, ±3.5%, ±4.0.%, ±4.5%, ±5.0%, ±6.0%, ±7.0%±, 8.0%, ±9.0%±, 10.0%, ±15.0%, or ±20.0%.

In this context, it is noted that the formation of complex (C) between a receptor binding reagent L and its receptor P, for example, a cell surface receptor molecule can be described by a two-state process noted $$C \rightleftharpoons P + L$$

The corresponding dissociation $K_d$ constant is defined as $$K_d = \frac{[P][L]}{[C]}$$

wherein [P], [L], and [C] are the equilibrium molar concentrations of the receptor, the receptor binding reagent (ligand) and the respective complex at a given temperature and pressure. The dissociation $K_d$ constant can also be expressed as the ratio of the constant of the on-rate ($k_{on}$) for the speed of association/formation (also called association rate constant) of the complex and the constant of the off-rate ($k_{off}$) for the dissociation of the complex (also called dissociation rate constant) with $$K_d = k_{off}/k_{on}$$

In the present application, the values of the thermodynamic and kinetic constants $K_d$, $K_a$, $k_{on}$ and $k_{off}$ refer to their determination under "standard conditions", i.e. a temperature of 25° C. and atmospheric pressure of 1.013 bar.

In the present invention, it has been found, as mentioned above, that the $k_{off}$ rate [s⁻¹] for the binding of the receptor binding reagent to the receptor molecule via its specific binding site B is the determinant for the reversibility of staining of a target cell by a respective receptor binding reagent that has a further binding partner C, wherein the binding partner C is able of being bound by a multimerization reagent as defined herein. The $k_{off}$ range can be chosen within a range, depending, for example, on the target cell to be stained and optionally to be purified and the respective experimental condition. Taking into account that the half-life $T_{1/2}$ of the complex (C) between the receptor binding reagent L and the receptor molecule P can be expressed as ln 2/$k_{off}$=0.693/$k_{off}$ with a $k_{off}$ of 0.5×10⁻⁴ sec⁻¹ it takes 13860 seconds or 231 minutes or 3.85 hours to reduce the concentration of the complex between the receptor binding reagent and the receptor molecule by half, assuming that the dilution is sufficient that rebinding of the dissociated receptor binding reagent to the receptor molecule can be neglected. For a $k_{off}$ rate of 1.0×10⁻⁴ sec⁻¹, it takes thus 6390 seconds (or only 106.5 minutes or 1.775 hours), for a $k_{off}$ of 2.0×10⁻⁴ sec⁻¹ it takes 3465 seconds (or 57 minutes. i.e. less than one 1 hour) and for a $k_{off}$ of 4.0×10⁻⁴ sec⁻¹ it takes 1732 seconds (or about 28 minutes) to achieve the same reduction in the concentration of the complex. Thus, for the washing that is carried out after the separation of the stained target cells from the other cells in the sample and after the disruption of multivalent complex formed between the multimerization reagent and the receptor binding reagent, the cell receptor binding reagent may be chosen depending on the sensitivity of the cell to be stained to external influences. For example, for a rather sensitive cell, a receptor binding reagent with a rather high $k_{off}$ rate of, for example, greater than 4.0× 10⁻⁴ sec⁻¹ may be used so that, after the disruption of the multivalent binding complexes, most of the receptor binding reagent can be removed within one hour (as illustrated above, within 56 minutes the concentration of the complexes is reduced to 25% of the original concentration, assuming that rebinding effects can be neglected due to sufficient dilution). For a more robust cell, a receptor binding reagent with a lower $k_{off}$ rate of, for example, 1.0×10⁻⁴ sec⁻¹, the dissociation of which needs accordingly much more time, may be used (in this case, 212 min or about 3 and a half hours are necessary to dissociate and remove 75% of the receptor molecule binding reagent). After dissociation of the multimerization reagent (for example, by means of an competitor that is able to disrupt the reversible bond between the binding partner C and the multimerization reagent), washing may also occur under constant gentle agitation for at least 2 times the half-life $T_{1/2}$ in a buffer volume diluting the employed receptor binding reagent to a concentration which is at least by a factor of 10 below the dissociation constant ($K_d$). The dissociated receptor binding reagent is then removed, for example, by sedimentation of the target cells, and discarding the supernatant. In an alternative embodiment, it is possible to repeat the above described washing once or twice or several times to remove the receptor binding reagent to near completion. In this context, it is noted that the term "washing" as used herein with reference to the stained target cells means that the stained target cells are (concomitantly with the disruption of the multivalent binding complexes or after disruption of the multivalent binding complexes) contacted with a sufficient amount of washing buffer, incubated with the washing buffer over a suitable period of time for dissociation of the receptor binding reagent from the receptor molecule and then separated from the washing buffer (which thereby removes the dissociated receptor binding reagent) by a suitable procedure, for example, sedimentation of the target cells and removal of the supernatant or, for example, filtration of the washing buffer. The washing is usually carried out in buffer that does not have an adverse effect on the viability or the status of the cells to be stained or isolated, i.e. the washing is performed under physiologically acceptable conditions (such as physiologically acceptable buffer, suitable temperature, for example, at 4° C., 15° C. or 25° C., (i.e. room temperature) etc.). Suitable experimental washing conditions can easily be determined empirically by the person of average skill in the art. For example, if the $k_{off}$ has a relatively high value close to 0.5×10⁻⁴ sec⁻¹, and the stained cells are (relatively) insensitive to higher temperature, the washing can be carried out at room temperature, to allow for a faster dissociation of the receptor binding reagent from the stained cells. Alternatively, if the stained cells are relatively sensitive to higher temperature, the washing might be carried out a 4° C., so that the dissociation/removal of the receptor binding reagent takes longer however the functional status or viability of the cells will not be affected. A temperature of 4° C. or at least below 15° C. is preferred in some embodiments to prevent any change of the physiological status of the target cells.

In this context, it is noted that the receptor binding reagent can either have a (any) single binding site B that specifically binds the receptor molecule or the receptor binding reagent can also have two or more such binding sites B, as long as binding of the receptor molecule via (each of) the binding site(s) B has an aggregate value of the $k_{off}$ of about 0.5×10⁻⁴ sec⁻¹ or greater. Thus, the receptor binding reagent can be monovalent (for example, a monovalent antibody fragment or a monovalent artificial binding molecule (proteinaceous or other) such as a mutein based on a polypeptide of the lipocalin family (also known as "Anticalin®"), or a bivalent molecule such as an antibody or a fragment in which both binding sites are retained such as an F(ab')$_2$ fragment. The receptor binding reagent might even be a pentameric IgM molecule, provided the $k_{off}$ rate of the whole IgM molecule is $0.5 \times 10^{-4}$ sec$^{-1}$ or greater.

The $k_{off}$-rate for the binding of the receptor binding reagent to the receptor molecule and, of course, also the $k_{on}$ rate can be determined via standard methods, such as surface plasmon resonance (SPR), for example, using the BIAcore technology (SPR; Jonsson, U. et al. (1991) Biotechniques, 11, 620-627). This determination is within the average knowledge of the person skilled in the art. Usually, the determination is carried out at 25° C. by surface plasmon resonance analysis, at a suitable concentration of the receptor binding reagent) with the receptor molecule being immobilized on the surface of a respective sensor chip. The ligand (i.e., the receptor binding reagent), for example, a Fab fragment is applied on the chip in different concentrations (usually around the estimated $K_d$ value as determined from preliminary characterizations), using flow rates in the range of µl/min.

As an illustrative example, it is referred in this context to the determination of the $k_{off}$ rate of the binding of CD4 (as a receptor molecule) to Fab fragments derived from the monoclonal antibody 13B8.2. As described in U.S. Pat. No. 7,482, 000 or in Bes, C., et al. *J Biol Chem* 278, 14265-14273 (2003), the $k_{off}$ rate and the other kinetic parameters can be determined at 25° C. by surface plasmon resonance analysis using a BIAcore 2000 instrument (BIAcore AB, Uppsala, Sweden). Recombinant CD4 can be covalently immobilized on a CM5 sensor chip surface using the amine coupling method according to the manufacturer's instructions. A control reference surface can be prepared using the same chemical treatment of the flow cell surface without injection of CD4. Recombinant Fab mutants in buffer containing 10 mM Hepes (pH 7.4), 3 mM EDTA, 150 mm NaCl, and 0.005% nonionic surfactant P20 (BIAcore AB) can then injected at concentrations between 5 and 20 µg/ml over the flow cell, and the dissociation phase will follow by a regeneration step with 5 mM HCl solution. The flow rate can be set to 30 µl/min. All the sensorgrams can be corrected by subtracting the signal from the control reference surface. The data can then be globally fitted to a 1:1 Langmuir binding isotherm using BIAevaluation Version 3.2 software.

As another illustrative example it is referred to the determination of the $k_{off}$ rate of anti-CD30 Fab fragments for the recombinant CD30A antigen fragment as measured by surface plasmon resonance by Schlapschy, M., et al. "Functional humanization of an anti-CD30 Fab fragment for the immunotherapy of Hodgkin's lymphoma using an in vitro evolution approach" *Protein Eng Des Sel* 17, 847-860 (2004). This determination was carried out on a BIAcore X system (BIAcore, Uppsala, Sweden). After buffer exchange to 10 mM sodium acetate pH 3.85 by gel filtration, purified CD30A were diluted to 50 µg/ml and immobilized on a 'research grade' CM5 sensor chip using the amine coupling kit (BIAcore), resulting in the immobilization of 1700 response units (RU). The purified recombinant Fab fragments were e applied in PBS/P (PBS containing 0.005% surfactant P-20; BIAcore) at a series of appropriate concentrations. Complex formation was observed under a continuous buffer flow of 5 µl/min. The sensorgrams were corrected by subtraction of the corresponding signals measured for the control blank channel, which was used in-line. The chip was regenerated by applying a 2 ml pulse of 1 mM NaOH at a flow-rate of 25 µl/min, followed by equilibration with PBS/P. Kinetic parameters can again be determined with BIAevalution software V 3.0 (BIAcore) using a 1:1 (Langmuir) binding model with drifting baseline.

Reverting to the method of the invention, as mentioned above, the affinity of the receptor binding reagent for the cell surface receptor molecule does not have to be of low affinity. Rather (see also the Experimental Section), the dissociation constant ($K_d$) for the binding between said receptor binding reagent and said receptor molecule can be the range of about $10^{-2}$ M to about $10^{-8}$ M, or of about $10^{-2}$ M to about $10^{-9}$ M, or of about $10^{-2}$ M to about $0.8 \times 10^{-9}$ M, or of about $10^{-2}$ M to about $0.6 \times 10^{-9}$ M, or of about $10^{-2}$ M to about $0.4 \times 10^{-9}$ M, or of about $10^{-2}$ M to about $0.3 \times 10^{-9}$ M, or of about $10^{-2}$ M to about $0.2 \times 10^{-9}$, or of about $10^{-2}$ M to about $0.15 \times 10^{-9}$ M, or of about $10^{-2}$ to about $10^{-10}$, as long as, after disruption of the multivalent binding complexes, the $k_{off}$ allows the removal of the receptor binding reagent in a time frame and under washing conditions that are acceptable for the cell to be stained or isolated. In one embodiment the dissociation constant ($K_d$) for the binding between said receptor binding reagent and said receptor molecule can be in the range of about $10^{-7}$ M to about $10^{-10}$ M, or of about $10^{-7}$ M to about $0.8 \times 10^{-9}$ M, or of about $10^{-7}$ M to about $0.6 \times 10^{-9}$ M, of about $10^{-7}$ M to about $0.3 \times 10^{-9}$ M, of $1.1 \times 10^{-7}$ M to about $10^{-10}$ M, or of about $1.1 \times 10^{-7}$ M to about $0.15 \times 10^{-9}$ M, or of about $1.1 \times 10^{-7}$ M to about $0.3 \times 10^{-9}$ M, or of about $1.1 \times 10^{-7}$ M to about $0.6 \times 10^{-9}$ M, or of about $1.1 \times 10^{-7}$ M to about $0.8 \times 10^{-9}$ M. In this context it is noted that $k_{on}$-rates up to about $5 \times 10^6$ M$^{-1}$ s$^{-1}$ are known for the binding of immunoglobulins such as antibodies or Fab-fragments to their respective antigen (see, for example, Lee et al., Mol. Biol. (2004) 340, 1073-1093, FIG. 4 in which the Fab fragment G6-23 has a $k_{on}$ rate of $5.6 \times 10^6$ M$^{-1}$ s$^{-1}$ or, for example, Kwong et al *J. Mol. Biol.* 2008 Dec. 31; 384(5): 1143-1156 or International Patent Application WO 2010/017103 which reports $k_{on}$ values of $1 \times 10^5$ M$^{-1}$s$^{-1}$ to $1.4 \times 10^6$ M$^{-1}$s$^{-1}$ for the Fab fragment of anti-human NKG2D monoclonal antibody and antibodies as IgG1 (see Table 1 of Kwong et al., supra). Accordingly, assuming a receptor binding reagent such as a Fab fragment has a $k_{on}$ value for the binding of the receptor molecule of $5 \times 10^6$ M$^{-1}$s$^{-1}$ and a $K_d$ of $1 \times 10^{-10}$ the $k_{off}$ is $5 \times 10^{-4}$ M, rendering such antibody molecules (or receptor binding reagents in general) well suitable for being used in the reversible staining method of the invention (with a $k_{off}$ of $5 \times 10^{-4}$ sec$^{-1}$ it takes only 1386 seconds or 23 minutes to reduce the concentration of the complex between the receptor binding reagent and the receptor molecule by half, despite an affinity with a $K_d$ of $1 \times 10^{-10}$ M). Likewise, as a further illustrative example, if the receptor binding reagent has a $k_{on}$ value for the binding of the receptor molecule of $5 \times 10^5$ M$^{-1}$ s$^{-1}$ and a $K_d$ of $1 \times 10^{-9}$ the $k_{off}$ is also $5 \times 10^{-4}$ M, resulting also in a rather fast dissociation of the receptor binding reagent from the target cell, after disruption of the multivalent binding complexes. In this context, it is possible, for example, by using evolutionary methods such as phage display to deliberately screen for receptor binding reagents such as antibody fragments or, for example, lipocalin muteins (cf. also Lee et al., supra in this regard). Thus, if wanted, receptor binding reagents with desired kinetic properties can be obtained by such evolutionary methods from a starting molecule of which the amino acid sequence is known. It is also possible to use in the method described here a receptor binding reagent that has a low affinity for the receptor molecule, the dissociation constant ($K_d$) for the binding between the receptor binding reagent and the receptor molecule may then be in the range of $10^{-2}$ to $10^{-7}$ M.

The staining method further comprises separating the stained cell from non-target cells present in a sample/mixture of cells. The separation can be carried out as described in U.S.

Pat. No. 7,776,562 or International Patent application WO 02/054065 and can further comprise removing said staining from said cell by disrupting the binding between the binding partner C of the receptor binding reagent and the binding sites Z of the multimerization reagent. This bond should be reversible, i.e. the bond should be capable of being disrupted under conditions suitable for carrying out the claimed method. The dissociation constant ($K_d$) for the binding between said binding partner C and said binding sites Z can, for example, be in the range of about $10^{-2}$ M to about $10^{-13}$ M. Thus, this reversible bond can, for example, have a $K_d$ of between about $10^{-2}$ M and about $10^{-13}$ M, or of between about $10^{-5}$ M and about $10^{-13}$ M, or of between about $10^{-6}$ M and about $10^{-10}$ M, or of between about $10^{-3}$ M and about $10^{-12}$ M or between about $10^{-4}$ M and $10^{-11}$ M, or between about $10^{-5}$ M and about $10^{-10}$ M. Also the $K_d$ of this bond can be determined by any suitable means, for example, by fluorescence titration, equilibrium dialysis or surface plasmon resonance as explained above in connection with the determination of the $k_{off}$ rate for the bond formed between the receptor binding reagent and the receptor molecule. The dissociation/removal of the staining of the multimerization reagent from the cells results in the removal of the dissociated receptor binding reagent, and thus of the whole multivalent binding complex including the detectable label from the previously stained cell. In order to facilitate the removal from the receptor binding reagent, a volume of a respective washing buffer might be used that brings the concentration of the added receptor binding reagent significantly below the $K_d$ for its interaction with the cognate receptor molecule. Alternatively, the washing might be repeated several times at lower volumes and gentle agitation might be desirable to prevent immediate rebinding. In one embodiment a volume of the washing buffer is used that lowers the concentration of the receptor binding reagent below the $K_d$ or even more preferably to a concentration below 1/10th of the $K_d$ so that more than 90% of the receptor binding reagent is present in the dissociated form (i.e. not bound to the receptor molecule) or even more preferably to a concentration below 1/100th of the $K_d$ so that more than 99% of the receptor binding reagent is present in the dissociated form or even more preferably to a concentration below 1/1000th of the $K_d$ so that more than 99.9% of the receptor binding reagent is present in the dissociated form.

In some embodiments of the invention, the receptor binding reagent is selected such that it comprises at least one binding partner C and the multimerization reagent comprises at least two binding sites Z, at least three or at least four binding sites Z for the binding partner C. In alternative embodiments, it is possible to use two different (kinds of) receptor binding reagents. Each of these two receptor binding reagents bind the same receptor molecule by a same or a different binding site B (for the latter case, it is possible that the two receptor binding reagent recognize and thus bind different epitopes on the same receptor molecule). In addition, each of the two receptor binding reagents has at least one binding partner C and the multimerization reagent has at least one binding site Z for the binding partner C of each of the two different receptor binding reagents. For example, it is possible to use two different receptor binding reagents, which both bind the same receptor molecule via the same binding site B but which have different binding partners C1 and C2. For example, one receptor binding reagent may have a binding partner C1 such as a hexa-histidine tag and the other receptor binding reagent has a binding partner C2 such as a FLAG tag. In such case, the multimerization reagent can comprise only one binding site (Z1) for the binding partner C1 and only one binding site for the binding partner C2. Since in total two binding sites are present in the multimerization reagent an avidity effect is still achieved. Such a multimerization reagent might, for example, be a biocompatible polymer (for example, dextrane or another polysaccharide) to which an Fab fragment of an anti-FLAG antibody and one Fab fragment of an anti-hexahistidine tag antibody is conjugated (for a detailed discussion of multimerization reagents see below). Regardless, of whether one or two receptor binding reagents with only one or two or more binding partners C are used in the invention, any combination of the binding partner C and the multimerization reagent can be chosen, as long as the binding partner C and the binding site(s) Z of the multimerization reagent are able to reversibly multimerize in a (multivalent) complex to cause an avidity effect, as also described in U.S. Pat. No. 7,776,562 or International Patent application WO02/054065.

In some illustrative embodiments the partners can be chosen from the following group:
(a) the binding partner C comprises biotin and the multimerization reagent comprises a streptavidin analog or an avidin analog that reversibly binds to biotin,
(b) the binding partner C comprises a biotin analog that reversibly binds to streptavidin or avidin and the multimerization reagent comprises streptavidin, avidin, a streptavidin analog, or an avidin analog that reversibly binds to said biotin analog, or
(c) the binding partner C comprises a streptavidin or avidin binding peptide and the multimerization reagent comprises streptavidin, avidin, a streptavidin analog, or an avidin analog that reversibly binds to said streptavidin or avidin binding peptide. In some of these embodiments, the binding partner C may comprise the streptavidin-binding peptide Trp-Ser-His-Pro-Gln-Phe-Glu-Lys (SEQ ID NO: 1) and said multimerization reagent comprises the streptavidin analog $Val^{44}$-$Thr^{45}$-$Ala^{46}$-$Arg^{47}$ (SEQ ID NO: 2) or the streptavidin analog $Ile^{44}$-$Gly^{45}$-$Ala^{46}$-$Arg^{47}$ (SEQ ID NO: 3) both of which are described in U.S. Pat. No. 6,103,493, for example, and are commercially available under the trademark Strep-Tactin®. The streptavidin binding peptides might, for example, be single peptides such as the "Strep-Tag®" described in U.S. Pat. No. 5,506,121, for example, or streptavidin binding peptides having a sequential arrangement of two or more individual binding modules as described in International Patent Publication WO 02/077018.

In other embodiments, in which only one binding partner C is used, the binding between the binding partner C and said at least 2 binding sites Z of said multimerization reagent occurs in the presence of a divalent cation. In an illustrative example of such an embodiment the binding partner C comprises a calmodulin binding peptide and the multimerization reagent comprises multimeric calmodulin as described in U.S. Pat. No. 5,985,658, for example. Alternatively, the binding partner C may comprise a FLAG peptide and said multimerization reagent may comprise an antibody binding to the FLAG peptide, e.g. the FLAG peptide, which binds to the monoclonal antibody 4E11 as described in U.S. Pat. No. 4,851,341. In yet another illustrative example the binding partner C comprises an oligohistidine tag and the multimerization reagent comprises an antibody or a transition metal ion binding the oligohistidine tag. The disruption of all these binding complexes may be accomplished by metal ion chelation, e.g. calcium chelation, e.g. by addition of EDTA or EGTA. Calmodulin, antibodies such as 4E11 or chelated metal ions or free chelators may be multimerized by conventional methods, e.g. by biotinylation and complexation with streptavidin or avidin or multimers thereof or by the introduction of carboxyl residues into a polysaccharide, e.g. dextran, essentially as described in Noguchi, A., Takahashi, T., Yamaguchi, T., Kitamura, K., Takakura, Y., Hashida, M. & Sezaki, H. (1992). "Preparation and properties of the immunoconjugate composed of anti-human colon cancer monoclonal antibody and mitomycin C dextran conjugate. Bioconjugate Chemistry 3, 132-137" in a first step and coupling of calmodulin or antibodies or chelated metal ions or free chelators via primary amino groups to the carboxyl groups in the polysaccharide, e.g. dextran, backbone using conventional carbodiimide chemistry in a second step.

In such embodiments the binding between said binding partner C and said at least two binding sites Z of said multimerization reagent can be disrupted by metal ion chelation. The metal ion chelation may, for example, be accomplished by addition of EDTA.

In the method of the invention it is also possible that the multimerization reagent is an oligomer or a polymer of streptavidin or avidin or of any analog of streptavidin or avidin. The oligomer or polymer may be crosslinked by a polysaccharide. In an embodiment oligomers or polymers of streptavidin or of avidin or of analogs of streptavidin or of avidin are prepared by the introduction of carboxyl residues into a polysaccharide, e.g. dextran, essentially as described in "Noguchi, A., Takahashi, T., Yamaguchi, T., Kitamura, K., Takakura, Y., Hashida, M. & Sezaki, H. (1992). Preparation and properties of the immunoconjugate composed of anti-human colon cancer monoclonal antibody and mitomycin C dextran conjugate. Bioconjugate Chemistry 3, 132-137" in a first step. Then streptavidin or avidin or analogs thereof are coupled via primary amino groups of internal lysine residue and/or the free N-terminus to the carboxyl groups in the dextran backbone using conventional carbodiimide chemistry in a second step. However, crosslinked oligomers or polymers of streptavidin or avidin or of any analog of streptavidin or avidin may also be obtained by crosslinking via bifunctional linkers such as glutardialdehyde or by other methods described in the literature.

In another embodiment of the staining method of the invention the binding partner C comprises an antigen and the multimerization reagent comprises an antibody or antibody fragment against said antigen. The antigen may, for example, be an epitope tag. Examples of suitable epitope tags include, but are not limited to, the Myc-tag (sequence: EQKLISEEDL, SEQ ID NO: 4), the HA-tag (sequence: YPYDVPDYA, SEQ ID NO: 5), the VSV-G-tag (sequence: YTDIEMNRLGK, SEQ ID NO: 6), the HSV-tag (sequence: QPELAPEDPED, SEQ ID NO: 7), the V5-tag (sequence: GKPIPNPLLGLDST, SEQ ID NO: 8) or glutathione-S-transferase (GST), to name only a few. In another embodiment, the binding partner C comprises maltose binding protein (MBP), chitin binding protein (CBP) or thioredoxin as an antigen. In these cases, the complex formed between the at least two binding sites Z of the multimerization reagent (antibody) and the antigen can be disrupted by adding the free antigen, i.e. the free peptide such as a Myc-tag or the HA-tag (epitope tag) or the free protein (such as MBP or CBP). In this context, it is noted that in case the FLAG-tag (sequence: DYKDDDDK, SEQ ID NO: 9) is used as binding partner C and the multimerization reagent comprises an antibody or antibody fragment binding the FLAG tag, it is also possible of disrupting this reversible bond by addition of the free FLAG peptide.

In the method of the invention the at least one binding site B of the receptor binding reagent which specifically binds to said receptor molecule can for example be an antibody or a divalent antibody fragment such as an (Fab)$_2$'-fragment, divalent single-chain Fv fragment. It might also be a bivalent proteinaceous artificial binding molecule such as a dimeric lipocalin mutein that is also known as "duocalin". In other embodiments the receptor binding reagent may have a single binding site B, i.e., may be monovalent. Examples of monovalent receptor binding reagents include, but are not limited to, a monovalent antibody fragment, a proteinaceous binding molecule with antibody-like binding properties or an MHC molecule.

Examples of monovalent antibody fragments include, but are not limited to an Fab fragment, an Fv fragment, and a single-chain Fv fragment (scFv).

Examples of proteinaceous binding molecules with antibody-like binding properties that can be used as receptor binding reagent that specifically binds the receptor molecule include, but are not limited to, an aptamer, a mutein based on a polypeptide of the lipocalin family, a glubody, a protein based on the ankyrin scaffold, a protein based on the crystalline scaffold, an adnectin, an avimer, a EGF-like domain, a Kringle-domain, a fibronectin type I domain, a fibronectin type II domain, a fibronectin type III domain, a PAN domain, a G1a domain, a SRCR domain, a Kunitz/Bovine pancreatic trypsin Inhibitor domain, tendamistat, a Kazal-type serine protease inhibitor domain, a Trefoil (P-type) domain, a von Willebrand factor type C domain, an Anaphylatoxin-like domain, a CUB domain, a thyroglobulin type I repeat, LDL-receptor class A domain, a Sushi domain, a Link domain, a Thrombospondin type I domain, an immunoglobulin domain or a an immunoglobulin-like domain (for example, domain antibodies or camel heavy chain antibodies), a C-type lectin domain, a MAM domain, a von Willebrand factor type A domain, a Somatomedin B domain, a WAP-type four disulfide core domain, a F5/8 type C domain, a Hemopexin domain, an SH2 domain, an SH3 domain, a Laminin-type EGF-like domain, a C2 domain, "Kappabodies" (Ill. et al. "Design and construction of a hybrid immunoglobulin domain with properties of both heavy and light chain variable regions" Protein Eng 10:949-57 (1997)), "Minibodies" (Martin et al. "The affinity-selection of a minibody polypeptide inhibitor of human interleukin-6" EMBO J 13:5303-9 (1994)), "Janusins" (Traunecker et al. "Bispecific single chain molecules (Janusins) target cytotoxic lymphocytes on HIV infected cells" EMBO J 10:3655-3659 (1991) and Traunecker et al. "Janusin: new molecular design for bispecific reagents" Int J Cancer Suppl 7:51-52 (1992), a nanobody, a adnectin, a tetranectin, a microbody, an affilin, an affibody or an ankyrin, a crystallin, a knottin, ubiquitin, a zinc-finger protein, an autofluorescent protein, an ankyrin or ankyrin repeat protein or a leucine-rich repeat protein, an avimer (Silverman, Lu Q, Bakker A, To W, Duguay A, Alba B M, Smith R, Rivas A, Li P, Le H, Whitehorn E, Moore K W, Swimmer C, Perlroth V, Vogt M, Kolkman J, Stemmer W P 2005, Nat Biotech, December; 23(12):1556-61, E-Publication in Nat Biotech. 2005 Nov. 20 edition); as well as multivalent avimer proteins evolved by exon shuffling of a family of human receptor domains as also described in Silverman J, Lu Q, Bakker A, To W, Duguay A, Alba B M, Smith R, Rivas A, Li P, Le H, Whitehorn E, Moore K W, Swimmer C, Perlroth V, Vogt M, Kolkman J, Stemmer W P, Nat Biotech, December; 23(12):1556-61, E-Publication in Nat. Biotechnology. 2005 Nov. 20 edition).

In the method of the invention, the contacting of the mixture that contains the target cell(s) with the receptor binding reagent and the multimerization reagent can be carried out at any suitable temperature, as described in U.S. Pat. No. 7,776, 562 or International Patent application WO 02/054065, for example. Typically, the contacting of the mixture containing the target cells with the receptor binding reagent and the multimerization reagent and later also the removal of said reagents may be carried out at such temperatures, at which substantially no activation and/or no signaling events occur, which might result in an alteration of the target cell, e.g. the T cell phenotype, in case a T cell is to be stained or isolated. In some more preferred embodiments the contacting is carried out at a temperature of ≤15° C. or carried out at a temperature of ≤4° C.

In the method of the invention, virtually any said target cell can be used that has at least one common receptor molecule that is used for staining or isolation of the target cell. In order to achieve an avidity effect, the receptor molecule is typically present in two or more copies on the surface of the target cell. In typical embodiments the target cell is a mammalian cell or a eukaryotic or prokaryotic cell. Likewise, the at least one common (specific) receptor which defines the target cell population may be any receptor against which a receptor binding reagent as described above may be directed. For example, the receptor may be an antigen defining a cell population or subpopulation, e.g. a population or subpopulation of blood cells, e.g. lymphocytes (e.g. T cells, T-helper cells, for example, $CD4^+$ T-helper cells, B cells or natural killer cells), monocytes, or stem cells, e.g. CD34-positive peripheral stem cells or Nanog or Oct-4 expressing stem cells. Examples of T-cells include cells such as CMV-specific CD8+ T-lymphocytes, cytotoxic T-cells, memory T-cells and regulatory T-cells (Treg). An illustrative example of Treg are $CD4^+$ $CD25^+CD45RA$ Treg cells and an illustrative example of memory T-cells are $CD62L^+CD8^+$ specific central memory T-cells. The receptor may also be a marker for tumor cells. In this context, it is noted that the term "target cells" as used herein encompasses all biological entities/vesicles in which a membrane (which can also be a lipid bilayer) separates the interior from the outside environment and which comprise specific receptor molecules on the surface of the biological entity. Examples of such entities include, but are not limited to, viruses, liposomes and organelles such as mitochondria, chloroplasts, the cell nucleus or lysosomes.

Once being isolated, the target cell population is characterized in that the receptor binding reagent has been substantially completely removed (typically below the detection limit as, for example as being detected by FACS) from said receptor. The complete removal of the receptor binding reagent is accomplished by using the reversibly multimerized receptor binding reagent having a high $k_{off}$ rate as described above. By so doing, a target cell population (defined by the common specific receptor) can be provided that has a functional status which has not been altered by the purification method.

The fact that the target cell population or any other population of a biological entity in which a membrane (which can also be a lipid bilayer) separates the interior from the outside environment and that is further characterized to comprise a common specific receptor molecule on the surface can be purified by the methods of the invention under subsequent removal of any used purification reagent (receptor binding reagent; multimerization reagent, label) offers—beyond the advantage that, if the target is a cell or an organelle, the physiological status is not altered—the regulatory advantage that the purification reagents are not administered to the patient during the use of such purified biological entities as medicaments. In such cases, regulatory authorities like FDA (USA) or EMEA (Europe) require less expensive constraints with respect to production processes for said purification reagents than in cases where the purification reagent is administered together with the medicament being a cell or a liposome. Therefore, a clear technical advantage exists also with respect to the methods of the invention for the purification of entities of which no physiological status can be manipulated like for liposomes, for example, if such liposomes have to be purified and are used as medicaments.

The label which is used for the detection of stained cells may be any label which is used in diagnostic and analytical methods. Preferably the label does not negatively affect the characteristics of the cells to be stained or isolated. Examples of labels are fluorescent labels (for example, phycoerythrin, allophycocyanin, coumarin or rhodamines to name only a few), magnetic labels, chromophoric labels, spin labels suitable for electron spin resonance/electron paramagnetic resonance (EPR), or radioactive labels. The label may be bound to the receptor binding reagent and/or the multimerization reagent. The label may be a direct label, i.e. a label bound to one of the members of the multivalent binding complex as specified above. In such a case, the label might, for example, be covalently coupled (conjugated) to either the receptor binding reagent or the multimerization reagent (cf. the multimerization reagent carrying a fluorescent label such as phycoerythrin shown in FIG. 1). Alternatively, the label may be an indirect label, i.e. a label which is bound to a further reagent which in turn is capable of binding to one of the members of the multivalent binding complex as specified above. Such a label may be added before, during or after the multivalent binding complex has been formed. An example for such an indirect label is a bis-, tris-, or tetrakis-NTA containing fluorescent dye as described by Lata et al., J. Am. Chem. Soc. 2005, 127, 10205-10215 or Huang et al., Bioconjugate Chem. 2006, 17, 1592-1600. Said label is able to bind non-covalently (via metal chelation) to an oligohistidine tag. Thus, in this example, the receptor binding reagent and/or the multimerization reagent may carry an oligohistidine tag (for example, a Fab fragment as receptor binding reagent that has an oligohistidine tag such as a hexa-histidine tag fused to the C-terminus of the CH1 or the CL-domain or a streptavidin mutein such as Strep-Tactin® as multimerization reagent that has an oligohistidine tag fused to the N- or C-terminus of one of its subunits can be used), thereby being enabled to non-covalently bind such a NTA based fluorescent dye compound described by Lata et al, supra or Huang et al, supra. Such a non-covalently binding label needs not necessarily be bound to its target (receptor binding reagent and/or the multimerization reagent) before the multivalent binding complex is formed but can also be added to the sample when the multivalent binding complex forms or after the multivalent binding complex has been formed. Such a non-covalently binding label can also be added after the multivalent binding complex is bound to the target cells. Instead of the NTA comprising fluorescent dye:oligohistidine tag binding pair described above, also any other specific binding pair such as, for example, digoxigenin and an anti digoxigenin antibody or antibody fragment carrying the fluorescent or other label can be used for indirect labeling. In such a case, the receptor binding reagent and/or the multimerization reagent is conjugated to/coupled with digoxigenin and an anti digoxigenin antibody or antibody fragment carrying the chosen label binds (via digoxigenin) to the multimerization reagent or the receptor binding reagent.

In embodiments of the method of the invention, a target cell is stained and optionally isolated by means of a group of at least two different (preselected) receptor molecules. Target cell isolation on behalf of more than one common receptor may be done by performing a method of the invention in a sequential manner by using corresponding receptor binding reagents in each cycle. In this case, the same label may be used for each cycle. Alternatively, simultaneous labeling of the target cells is possible when different labels are used for each receptor molecule. Such a sequential cell enrichment and/or (simultaneous) multiparameter staining uses at least two different receptor binding reagents, each receptor binding reagent comprising at least one binding site B which specifically binds to a preselected receptor molecule of a group of at least two different receptor molecules. Illustratively speaking, the at least two different receptor molecules may be different CD markers such as $CD4^+CD25^+$ T regulatory cells, or $CD62L^+CD8^+$ specific central memory T-cells. The cells can, for example, be antigen-specific T-cells such as CMV-specific $CD8^+$ T cells which can be isolated by first selecting $CD8^+$ T-cells, followed by a second staining and isolation for the CMV-specific target population such as HLA-B8/IE1K$_{199-207}$-specific $CD8^+$ T-cells.

In such embodiments the receptor binding reagent that binds to the second or any further receptor molecule of the group of at least two different receptor molecules may further comprise at least one binding partner C.

For the staining of this second receptor molecule, the dissociation rate constant $k_{off}$ for the binding between the receptor binding reagent that specifically binds via the binding site B and said second or any further receptor molecule may also have (like the receptor binding reagent that binds the first receptor molecule) a $k_{off}$ rate of $0.5 \times 10^{-4}$ sec$^{-1}$ or greater. Alternatively, in line with the method of U.S. Pat. No. 7,776,562 or International Patent application WO 02/054065, the dissociation constant ($K_d$) for the binding between said second or any further receptor molecule and said receptor binding reagent that specifically binds said second or any further receptor molecule may be in the range of $10^{-2}$ to $10^{-7}$ M.

As discussed above the staining method of the invention can be used for the isolation of a cell population that is defined by the presence of at least one common specific receptor molecule. The cell population that is defined by the presence of a common specific receptor molecule may, for example, a T-cell population, including for example, an antigen-specific T cell population. This purified cell population can for example be used for adoptive transfer or immunotherapy.

The method of the invention can also be used for the determination of the functional status of a T cell population, or for the purification of a T cell population for in vitro expansion.

In more detail and in accordance with the disclosure of U.S. Pat. No. 7,776,562, the method of the present invention allows a functional isolation of target cell populations, e.g. of T cell populations based on a reversible staining procedure. The original functional status of target cells, e.g. T cells, can be substantially maintained after the identification and purification. Thus, the method of the invention is of broad benefit for basic research and clinical applications.

Examples of preferred applications are as follows:
Basic Research:
Direct ex vivo investigation of the functional status of lymphocytes such as T-cells including, for example, antigen specific T cell populations. The functional status of T cell populations in vivo is suggested to be highly diverse and dependent on specific in vivo conditions, but because of the lack of appropriate investigative tools, these aspects are only marginally understood. With, for example, Fab multimers as described here, epitope-specific T cell populations can be identified and purified independent of their functional status. However, the binding of irreversible reagents interferes with subsequent functional assays. Reversible T cell staining e.g. using Fab-fragments equipped with a streptavidin binding peptide/Strep-Tactin® reagents is a technology allowing the direct functional ex vivo investigation of unaltered diverse T cell populations.

Purification of T cell populations for highly efficient in vitro expansion. The characterization of T cell populations obtained ex vivo often requires further in vitro expansion to T cell lines or T cell clones.

With Fab multimer techniques, single cells or distinct phenotypic subpopulations within a diverse T cell population can be isolated, but the binding of the reagents to the TCR interferes with the efficiency of in vitro expansion. This experimental problem is solved by reversible T cell staining using the reagents of the invention, e.g. Fab-Strep-Tag®/Strep-Tactin® reagents. Such Fab fragments might carry as binding partner C a streptavidin binding peptide having a sequential arrangement of two or more individual binding modules as described in International Patent Publication WO 02/077018.

Purification of T cell populations for adoptive transfer experiments. Many in vivo experiments in immunological research require the adoptive transfer of purified T cells into recipient animals. Both, the purity of the transferred T cell populations and possible changes in the cells that occur during the isolation procedure are concerns in these experimental systems. The highest purity of cell populations is achieved by positive selection methods, but the markers (usually antibodies) used for identification are difficult to remove from the surface of isolated cells and can interfere with the outcome of subsequent in vivo experiments.

Reversible T cell staining using reagents of the invention, e.g. Fab Strep-Tag®/Strep-Tactin® reagents allows the combination of positive selection methods with later removal of the selection marker and might greatly improve adoptive transfer experiments.

Clinical Applications:
Purification of T cell populations for highly efficient in vitro expansion. Generation of human T cell lines or clones (e.g. pathogen/tumor-specific or autoreactive T cells) is necessary in many areas of clinical research, diagnostics, and immunotherapy. In vitro culture is often limited by difficulties in standardizing conditions for antigen-specific stimulation. Improved strategies for the purification of T cell populations could greatly enhance the efficiency of in vitro expansion, allowing the use of antigen-independent stimulation such as mitogens and anti-CD3. With the invention, e.g. with MHC-Strep-Tag® or Fab-Strep-Tag® reagents (as receptor binding reagent) and a Strep-Tactin® multimerization reagent, T cell populations can be isolated directly ex vivo and expanded in vitro after dissociation of the reagents. This approach is expected to be much more efficient than purification using, for example, conventional irreversible MHC multimer reagents, as the binding of the reagents negatively interferes with the efficiency of in vitro T cell expansion.

Purification of T cell populations from in vitro expanded cell lines or clones for further functional analyses or therapy. In vitro expansion of T cells requires the addition of antigen-presenting cells or feeder cells to the culture. For further functional analysis, and especially for therapeutic applications (e.g. adoptive transfer), it would be helpful to remove these contaminating cells. For positive selection procedures (which usually result in the highest degrees of purity), the selection marker should be removable from the T cell surface, as it might interfere with functional assays or adoptive transfer. If T cells are used for in vivo applications the selection marker must be further removed if it contains substances that could cause clinical complications such as allergic reactions. Reversible T cell staining e.g. using MHC-Strep-Tag® or Fab-Strep-Tag® reagents/Strep-Tactin® reagents fulfills all these criteria.

Ex vivo purification of T cell populations for "direct adoptive immunotherapy". The isolation of T cell populations directly ex vivo followed by immediate transfer of the cells into recipients (without any further in vitro propagation) is of special clinical interest. It is expected that directly isolated cell populations are much more efficient than cultured cells for in vivo applications. Extremely high numbers of in vitro expanded T cells are required for effective adoptive transfers, a phenomenon most likely due to the adaptation of T cells to in vitro culture conditions. An example for an important clinical application for this procedure is the parallel purification and adoptive transfer of EBV and/or CMV-specific T cell populations during [otherwise] T cell-depleted stem cell transplantations, a protocol which is likely to dramatically reduce the incidence of EBV and CMV-related malignancies in transplant patients. Reversible T cell staining and isolation e.g. using MHC-Strep-Tag® or Fab-Strep-Tag® as receptor binding reagents and Strep-Tactin® as multimerization reagent is a very suitable method for these clinical applications. For example, MHC I molecules (fused to a streptavidin binding peptide) allow isolation of CMV-specific CD8+ T-cells in high purity from donor blood leukocytes; subsequently such purified cells are directly transferred to immunocompromised patients suffering from life threatening CMV disease (e.g. upon allogeneic stem cell transplantation). Cf. Schmitt et al., (2011) TRANSFUSION, Volume 51, pp. 591-599 in this respect. Other examples include purified Treg cell population for use in adoptive transfer for treatment of autoimmune diseases such as graft-versus-host disease (GvHD) or graft rejection, or Type 1 diabetes, colitis or allergy. For this purpose, the Treg target cell population may be CD4$^+$CD25$^+$CD45RA$^+$ Treg cells which are stained/isolated in a sequential manner using three receptor binding reagents such as Fab fragments that specifically bind the CD4 receptor molecule, the CD25 receptor molecule or the CD45RA receptor molecule. Other examples include the isolation of natural killer cells via the CD56 receptor molecule (also known as Neural Cell Adhesion Molecule (NCAM)) or of hematopoietic stem cells such as CD34$^+$, CD59$^+$, Thy1/CD90$^+$, CD38$^{lo/-}$, CD133$^+$ or Ckit/CD117$^+$ hematopoietic stem cells via the respective cell surface receptor molecule.

Functional T Cell Diagnostics.

MHC multimer techniques allow quantification and phenotypic characterization of antigen-specific T cells directly ex vivo. However, binding of multimer reagents to the TCR complicates the use of purified cells in functional assays (e.g. chronic virus infections [HIV, CMV, EBV, HBV, HCV], tumor-specific T cell populations).

Reversible T cell staining and isolation e.g. using Fab-Strep-Tag®/Strep-Tactin® reagents opens the door for powerful evaluation of such T cell status in many clinical situations.

The invention will be further illustrated by the following experimental Examples.

EXAMPLES

Materials and Methods

Blood Samples

Fresh PBMCs were generated from either peripheral blood or buffy-coats by centrifugation over Biocoll separating solution. Peripheral blood was obtained from healthy adult donors at the Institute of Medical Microbiology, Immunology and Hygiene (Technical University Munich), and buffy-coats were obtained from autologous blood donors at the Institute for Anesthesiology, German Heart Centre Munich (State of Bavaria and Technical University Munich). Written informed consent was obtained from the donors, and usage of the blood samples was approved according to national law by the local Institutional Review Board (Ethikkommission der Medizinischen Fakultät der Technischen Universität Munchen).

Production of Fab-Fragments as Receptor Binding Reagents (Cloning, Expression, Purification)

The variable domains originating from the monoclonal anti CD4 antibody 13B8.2 were generated by gene synthesis using the sequences described in U.S. Pat. No. 7,482,000 and Bes, C., et al. J Biol Chem 278, 14265-14273 (2003). The obtained variable sequences were subsequently joined with sequences coding for the human constant region Ch1 type 1 for the heavy chain and kappa for the light chain, and the heavy chain was carboxy-terminally fused with a sequential arrangement of two streptavidin binding modules (SAWSHPQFEK(GGGS)$_2$GGSAWSHPQFEK, SEQ ID NO: 10), commercially available as One-STrEP-tag affinity tag from IBA GmbH, Göttingen, Germany. All cloning was done using the StarGate® cloning system (IBA GmbH, Göttingen, Germany) with fusion vectors adapted for the described Fab expression. Mutagenesis PCR was applied to introduce amino acid substitutions. Following cloning, the Fab-One-STrEP-tag fusion proteins were expressed in *E. coli* strain JM83 (Plückthun, A. & Skerra, A. Expression of functional antibody Fv and Fab fragments in *Escherichia coli*. *Methods Enzymol* 178, 497-515 (1989)). After periplasmatic expression, the Fab-fragments were purified by One-STrEP-tag/Strep-Tactin® affinity chromatography (Schmidt, T. G. & Skerra, A. The Strep-Tag® system for one-step purification and high-affinity detection or capturing of proteins. *Nat Protoc* 2, 1528-1535 (2007)) via a Strep-Tactin® Superflow column (IBA), deliberated from desthiobiotin used for the elution of the respective Fab from the column by dialysis and thereby transferred into PBS pH 7.4 buffer and stored in PBS pH 7.4 at 4° C. or frozen (−20° C.) until use.

Multimerization, Staining and FACS Analysis

For staining of a CD4 receptor molecule specific target cell population in a mixture of cells, Strep-Tactin® labeled with phycoerythrine as a fluorescent label (IBA GmbH, Göttingen, Germany) was used as multimerization reagent together with the monomeric CD4 binding Fab-One-STrEP fragment of the variants of the antibody 13B8.2 (that served as receptor binding reagent) as described below. For FACS analysis 5×10$^6$ PBMCs were incubated with Fab multimers consisting of 0.2 µg Fab-fragment (comprising binding site B) equipped with the One-STrEP-tag (binding partner C) as receptor binding reagent and 0.75 µg Strep-Tactin® PE (IBA GmbH, Göttingen, Germany) as multimerization reagent using the protocol below. In addition, after FACS separation, the multivalent complexes were disrupted in a portion of each of the stained cells by addition of biotin as described below. Control antibody stainings were performed by concomitant application of the respective antibody: anti-CD4 (OKT4) (from eBiosciences, San Diego, Calif., USA). After the staining procedure of the present invention, cells were subsequently stained with propidium iodide for live/dead discrimination.

Protocol for Staining of 5×10$^6$ Cells with Receptor Binding Reagent and Multimerization Reagent 1. 0.75 µg Strep-Tactin PE were incubated with 0.2 µg monomeric CD4 binding Fab-One-STrEP fragment for 30 minutes at 4° C. in the dark.

2. 5×10$^6$ pre-cooled cells were washed with 10 ml Buffer IS (0.5% BSA (w/v) in phosphate buffered saline (PBS) pH 7.4 with PBS=8.06 mM Na$_2$HPO$_4$ 1.47 mM KH$_2$PO$_4$, 137 mM NaCl) in a 15 ml reaction tube to remove potentially existing ingredients like, e.g., D-biotin, which interfere with the subsequent procedure.

3. The cells were resuspended in 50 µl Buffer IS and transferred to a reaction vessel suitable for staining, e.g. a 96-well round bottom microtiterplate.
4. The pre-incubated Fab-Streptamer preparation from step 1 was added to the cells and mixed thoroughly by gentle pipetting.
5. The mixture was incubated for 20 minutes at 4° C. in the dark.
6. The cells were washed three times by centrifugation (400× g, 2 min) in 200 µl Buffer IS.
7. Cells were now ready for FACS-analysis or FACS-sorting. FACS analysis was carried out on a CyAn ADP Lx (Beckman Coulter) and analyzed with FlowJo software (TreeStar).

Protocol for Dissociation of Multivalent Complexes and Subsequent Removal of Receptor Binding Reagent from 5×10⁶ Cells with D-Biotin 1. 5×10⁶ stained cells (see above) were collected by centrifugation (400×g) and resuspended in 3 ml Buffer IS containing 1 mM D-biotin and incubated for 10 minutes at 4° C.
2. The cells were sedimented by centrifugation and the supernatant discarded.
3. Steps 1 and 2 were repeated.
4. The cells were resuspended in 10 ml Buffer IS and incubated for 10 minutes at 25° C. (for dissociation of the CD4 binding Fab fragment used as receptor binding reagent).
5. The cells were sedimented by centrifugation and the supernatant discarded.
6. Steps 4 and 5 were repeated three times.

Results

Principle of Reversible Fab-Multimer Staining

The basis of the present invention was the surprising discovery that receptor binding reagents such as monomeric Fab molecules having high affinities for the cell receptor with a $K_d < 10^{-7}$ down to $10^{-10}$ M need to be multimerized by a multimerization reagent for stable binding to the target cells and can be completely removed from the cell surface upon targeted disruption of the interaction between partner C and binding sites Z of the multimerization reagent (FIG. 1). It was further discovered that the key molecular basis for such reversible staining is not the affinity constant $K_d$ for the interaction between the cell surface receptor molecule and binding site B on the receptor binding reagent but the off rate for the dissociation of the receptor binding reagent from the receptor molecule. The off rate should be $0.5 \times 10^{-4} \text{ sec}^{-1}$ or higher for that a receptor molecule binding reagent can be completely removed from the target cell within a reasonable time window.

In order to demonstrate the key finding that the off rate and not the affinity is the essential parameter for performing reversible Fab-multimer staining, the following recombinant Fab-fragments (serving as the receptor binding reagents) directed against the cell surface receptor molecule CD4 were generated:

1) An Fab fragment consisting of the variable domain of the CD4 binding murine antibody 13B8.2 and a constant domain consisting of constant human CH1 domain of type gamma1 for the heavy chain (SEQ ID NO: 11) and the constant human light chain domain of type kappa (SEQ ID NO: 12), as described in U.S. Pat. No. 7,482,000. This Fab is denoted in the following 13B8.2 Fab fragment.

2) A mutant 13B8.2 Fab fragment in which the Phe residue at position 100 of the heavy chain was mutated to Ala (SEQ ID NO: 13) (referred to herein also as CD4 mutant 1 (F100A) and referred in U.S. Pat. No. 7,482,000, Table II, as F100K-H)
3) A mutant 13B8.2 Fab fragment in which the Tyr residue at position 92 of the light chain was mutated to Ala (SEQ ID NO: 14) (referred to herein also as CD4 mutant 2 (Y92A) and referred in U.S. Pat. No. 7,482,000, Table III, as Y92-L)
4) A mutant 13B8.2 Fab fragment in which the His residue at position 35 of the heavy chain was mutated to Ala (SEQ ID NO: 15) (referred to herein also as CD4 mutant 3 (H35A) and referred in U.S. Pat. No. 7,482,000, Table II, as H35-H)
5) A mutant 13B8.2 Fab fragment in which the His residue at position 91 of the light chain was mutated to Ala (SEQ ID NO: 16) (referred to herein also as CD4 mutant 4 (H91A) and referred in U.S. Pat. No. 7,482,000, Table III, as H91-L)

These Fab fragments have a broad spectrum of affinities ($K_d$ values ranging from 12.5 nM to 16.9 µM) and increasing $k_{off}$-rates; a summary of binding kinetics determined by BIAcore is listed in the following Table 1.

TABLE 1 binding kinetics between immobilized CD4 and the Fab fragment of CD4 binding antibody 13B8.2 and mutants Fab fragments from U.S. Pat. No. 7,482,000 and Bes, C., et al.. *J Biol Chem* 278, 14265-14273 (2003)

| Fab fragment | $k_{on}$ ($10^4 \text{ s}^{-1}\text{M}^{-1}$) | $k_{off}$ ($10^{-4} \text{s}^{-1}$) | $K_d$ (nM) |
|---|---|---|---|
| CD4 wt (13B8.2) | $0.37 \pm 0.09$ [1] | $1.11 \pm 0.4$ [1] | $29.17 \pm 3.27$ [1] |
| CD4 mutant 1 (F100A) | $0.562 \pm 0.003$ [2] | $4.75 \pm 0.05$ [2] | $845.1 \pm 47.5$ [2] |
| CD4 mutant 2 (Y92A) | $7.27 \pm 0.2$ [3] | $10.80 \pm 1.91$ [3] | $14.75 \pm 2.25$ [3] |
| CD4 mutant 3 (H35A) | $0.0301 \pm 0.200$ [2] | $18.90 \pm 0.85$ [2] | $6279.1 \pm 4240$ [2] |
| CD4 mutant 4 (H91A) | $0.0239 \pm 0.002$ [2] | $40.40 \pm 0.28$ [2] | $16903.7 \pm 1900$ [2] |

[1] This value is the arithmetic mean of the 3 measurements given in Bes, et al.,
[2] Value of single measurement as given in Bes et al.,
[3] Value is the arithmetic mean of the 2 measurements given in Bes et al., In order to introduce a binding partner C, the heavy chains of CD4 binding Fab-fragments were genetically fused to a tandem arrangement of two Strep-Tag®II sequences (SAWSHPQFEK(GGGS)₂GGSAWSHPQFEK, SEQ ID NO: 10, commercially available as OneSTrEP-tag sequence from IBA GmbH, Göttingen, Germany), and both chains were simultaneously expressed in the periplasm of *E. coli*. The functionally assembled Fab-fragments that served as receptor binding reagent were then purified by affinity chromatography on a Strep-Tactin® resin and, after removal of desthiobiotin by dialysis, subsequently multimerized in the presence of water-soluble phycoerythrin-labeled Strep-Tactin® (Strep-Tactin® PE, which serves as multimerization reagent providing at least 2 (about 12) binding sites Z for the One-STrEP-tag sequence, with phycoerythrin serving as a (fluorescent) label). The interaction between the streptavidin binding peptide and the streptavidin mutein "Strep-Tactin®" is reversible upon addition of D-biotin (or its derivatives such as diaminobiotin or desthiobiotin, for example) as a competing ligand.

Figure 2:
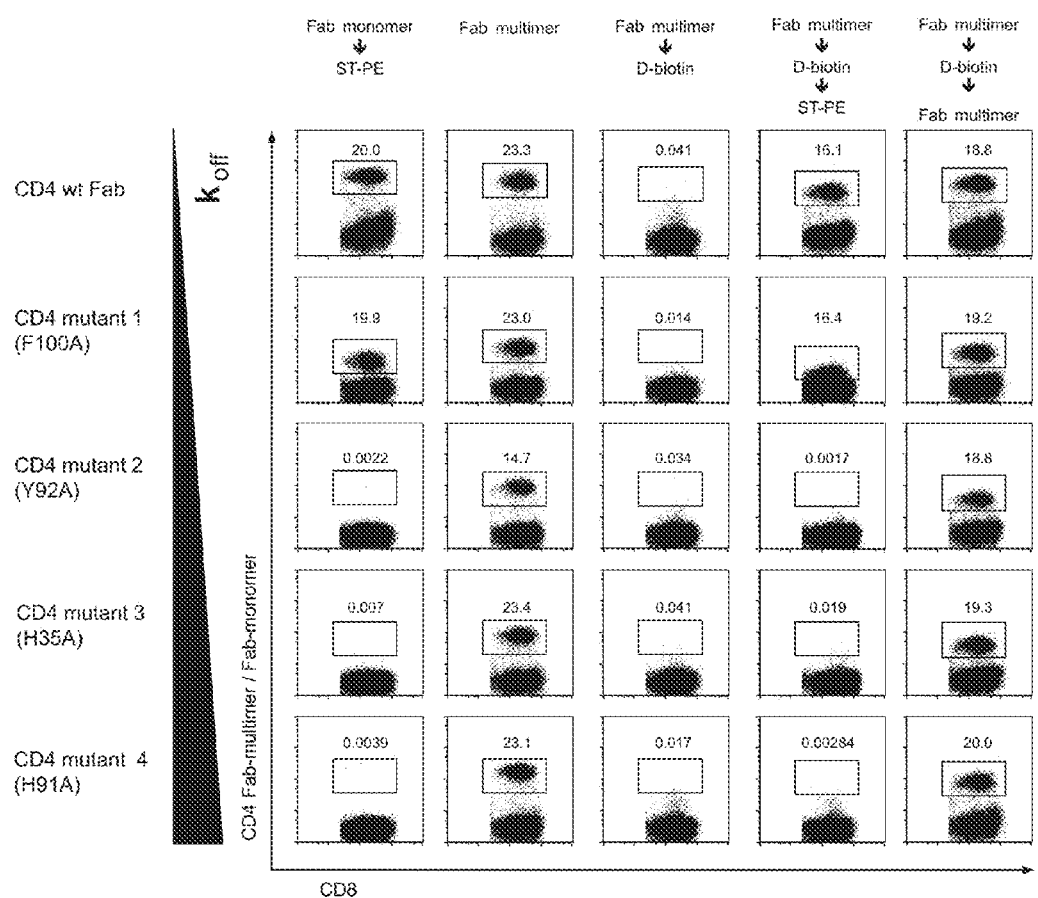
FIG. 2 shows the binding characteristics required for reversible Fab-multimer staining.

For staining and dissociation experiments, 5×10⁶ PBMCs were incubated with the respective anti-CD4 Fab-multimer-Strep-Tactin® PE complexes or with the corresponding Fab-monomers (the latter not complexed with Strep-Tactin® PE). Whereas the 13B8.2 wildtype (wt) Fab fragment and all mutants showed essentially equally good staining signals when multimerized, only the 13B8.2 wt Fab fragment and mutant 1, with slower $k_{off}$-rates ($1.11 \times 10^{-4}$ s$^{-1}$ and $4.75 \times 10^{-4}$ s$^{-1}$), were able to bind to their antigen in a monomeric state (FIG. 2, first and second columns). After D-biotin-mediated disruption of the multimeric complexes (FIG. 2, third column) and subsequent washing, the cells were probed for residual surface-bound Fab fragments by the addition of Strep-Tactin® PE alone (without bound Fab) (FIG. 2, fourth column). As expected from the monomer staining experiments, no remaining Fab monomers could be detected for mutants 2, 3 and 4, whereas substantial residual cell surface bound Fab of the wild-type and mutant 1 variants was observed. For mutants 2, 3 and 4, cells could be efficiently re-stained a second time using Fab-multimer labeling once again (FIG. 2, fifth column) demonstrating consistent biotin removal during detection of residual Fab fragments on the cell surface.

Figure 3:
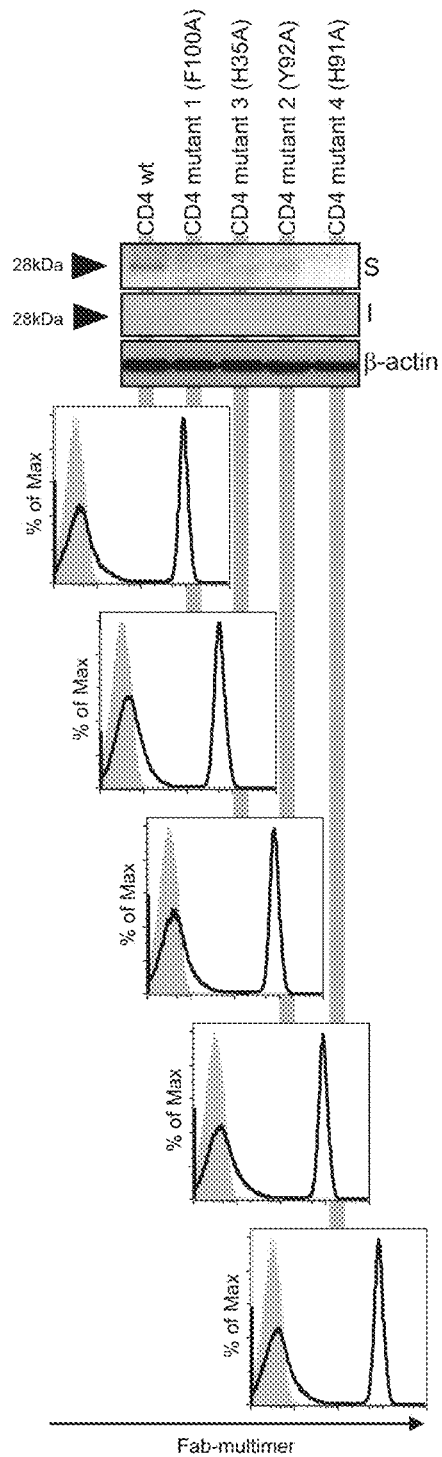
FIG. 3 shows, alternatively to the FACS analysis of FIG. 2, a Western blot analysis of reversibility of Fab-multimer staining. CD4 Fab-multimers were generated with the different anti-CD4 Fab-mutants listed in Table 1 and further specified in FIG. 2 and Strep-Tactin® PE (IBA GmbH, Göttingen, Germany). PBMCs were incubated with the different CD4 Fab-multimers and consistent cell staining in each sample was verified by flow cytometry (solid line compared to the tinted histogram representing unstained cells). Then, cells were treated with D-biotin and subsequently washed. Finally, washed cells were lysed, and the soluble (S) and insoluble (I) fractions were analyzed for remaining Fab-monomers using highly specific anti-Strep-Tag® antibodies (StrepMAB-Classic Horse Radish Peroxidase (HRP) conjugate; IBA GmbH, Göttingen, Germany). To control application of consistent amounts of insoluble cell material, β-actin was detected simultaneously with a primary antibody against β-actin from rabbit (Santa Cruz Biotechnology Inc., Santa Cruz, USA) and a secondary antibody against rabbit Ig (immunoglobulin) conjugated to HRP (Sigma, St. Louis, USA).

In addition to flow cytometry-based analysis (FIG. 2), complete removal of Fab-multimers was also assessed by an independent other analysis method, i.e. Western blot analysis (FIG. 3). Confirming the highly sensitive FACS results shown in FIG. 2, no Fab-fragments could be detected in either the soluble or the insoluble cell fraction after cell lysis for mutants 2, 3, and 4 while the wild type Fab fragment could be readily detected in the soluble fraction. As this experiment would also have detected internalized Fab fragments, which would not have been detected by FACS, any significant internalization of surface-bound receptor binding reagents during the staining and release procedure could be ruled out, thereby confirming correct interpretation of the results shown in FIG. 2. In contrast to the FACS experiment demonstrating incomplete removal of mutant 1 under the used washing conditions, remaining mutant 1 could not be detected in similarly treated cells by the Western blot experiment, presumably due to the inferior sensitivity of the Western blot method.

The main surprising result is the following: While, due to their low affinity ($K_d$ of about 6.2 µM and 16 µM) the complete release for Fab mutants 3 and 4 after disruption of the multivalent complex of the respective Fab fragment and Strep-Tactin® PE as the multimerization reagent was in line with the teaching of U.S. Pat. No. 7,776,562 or International Patent application WO02/054065, the complete release of the mutant 2 Fab-fragment in contrast to monomeric wild-type Fab molecules (and similar to the mutants 3 and 4 Fab fragments) was completely unexpected, since the affinity ($K_d$=14.75±2.25 nM) of mutant 2 was determined to be significantly higher than for the wild-type ($K_d$=29.17±3.27 nM) and than for all other mutants. However, mutant 2 is characterized by a much faster off-rate ($k_{off}$=10.80±1.91×10$^{-4}$ s$^{-1}$; see also Table 1) than the wild-type Fab fragment and Fab mutant 1, showing that the rate of dissociation has a dominating effect on the binding stability of surface-bound, monomeric Fab-fragments and not the affinity constant. In line with this interpretation, all fully reversible Fab-fragments (mutants 2-4) (which are the receptor binding reagents as defined herein) share a fast $k_{off}$-rate that is greater than $0.5 \times 10^{-4}$ s$^{-1}$. However, it should also be noted here that, during disruption of the multivalent binding complexes, with longer washing/incubation with the D-biotin containing solution, complete reversal of the binding of the wild type Fab fragment and Fab mutant 1—which both also have a $k_{off}$-rate that is greater than $0.5 \times 10^{-4}$ s$^{-1}$—is possible within a reasonable time window and thus can be used as receptor binding reagents in accordance with the invention.

In summary, these data demonstrate that multimerized receptor binding reagents with a $k_{off}$-rate for the binding of a receptor molecule via the binding site B that is greater than $0.5 \times 10^{-4}$ sec$^{-1}$ (for example Fab-fragments) can be used to stain cells in a stable manner and that these reagents can be completely detached and removed from the surface of labeled cells under physiological conditions.

The invention illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method of treating a subject with a population of target cells that is defined by the presence of a specific receptor molecule on the surface, the method comprising administering the population of target cells to the subject, wherein the population of target cells is isolated by a method of reversibly staining the target cells with a detectable label, the method of reversibly staining comprising:

contacting a mixture of cells comprising said target cells with (i) a receptor binding reagent, the receptor binding reagent comprising at least one binding site B, wherein the binding site B specifically binds to said receptor molecule, wherein the dissociation rate constant ($k_{off}$) for the binding between said receptor binding reagent via the binding site B and said receptor molecule has a value of about $0.5 \times 10^{-4}$ sec$^{-1}$ or greater, the receptor binding reagent further comprising at least one binding partner C, wherein the binding partner C is able of being reversibly bound to a binding site Z of a multimerization reagent, (ii) a multimerization reagent, the multimerization reagent comprising at least two binding sites Z for the reversible binding of the binding partner C of the receptor binding reagent, wherein the receptor binding reagent (i) and the multimerization reagent (ii) form multivalent binding complexes that bind to said target cell, each multivalent binding complex comprising at least two of said receptor binding reagents bound to one said multimerization reagent, said multivalent binding complex providing increased avidity, relative to said receptor binding reagent; and (iii) said detectable label bound or capable of binding to said multivalent binding complex, wherein said target cells are stained by binding of said multivalent binding complex to said target cells, and wherein staining of said target cell is reversible upon disruption of the binding between said binding partner C of said receptor binding reagent and said binding sites Z of said multimerization reagent.

2. The method of claim 1, further comprising purifying the population of target cells.

3. The method of claim 2, wherein the purified population of target cells is a mammalian cell population.

4. The method of claim 3, wherein said purified mammalian cell population is a lymphocyte population or a stem cell population.

5. The use of claim 4, wherein the lymphocyte population is an antigen-specific T cell population, a T-helper cell population, a B cell population or a natural killer cell population.

6. The method of claim 5, wherein the T-cell population is selected from the group of a CMV-specific CD8+ T-lymphocyte population, a cytotoxic T-cell population, a memory T-cell population, an in vitro engineered T-cell population and a regulatory T-cell population.

7. The method of claim 4, wherein the purified lymphocyte population is expanded in vitro.

8. The method of claim 4, wherein the purified stem cell population is administered to the subject for regenerative therapy.

9. The method of claim 8, wherein the stem cell population is a $CD34^+$ specific population or a $Nanog^+$ population.

10. The method of claim 4, wherein the purified cell population is a $CD4^+$ T-helper cell population.

11. The method of claim 10, wherein the CD4+ T-helper cell population is administered to the subject for modulating the immune response.

12. The method of claim 4, wherein the purified lymphocyte population is administered to the subject for a treatment selected from the group consisting of adoptive transfer, cancer therapy, treatment of bacterial infection, treatment of viral infection, or immunotherapy.

13. The method of claim 12, wherein the purified cell population is selected from the group consisting of $CD8^+$ T cells specific for an associated antigen, $CD8^+$ T cells specific for a leukemia-associated antigen, $CD8^+$ T cell specific for a melanoma-associated antigen, and $CD8^+$ T cells specific for a viral antigen.

14. The method of claim 13, wherein the $CD8^+$ T cells specific for a viral antigen are cytomegalovirus (CMV) phosphoprotein 65-specific CD8+ T cells or Epstein Barr Virus-EBNA antigen-specific CD8+ T cells.

15. The method of claim 4, wherein the purified cell population are Treg cells.

16. The method of claim 15, wherein the Treg cells are administered to the subject for treating a disease selected from the group consisting of an autoimmune disease, Type 1 diabetes, colitis, and an allergy.

17. The method of claim 16, wherein the autoimmune disease is graft-versus-host disease (GvHD) or graft rejection.

18. The method of claim 16, wherein the Treg cell population are $CD4^+CD25^+$. $CD45RA^+$ Treg cells.

19. The method of claim 4, wherein the purified cell population are $CD62L^+CD8^+$ specific central memory T-cells.

20. The method of claim 1, wherein the dissociation constant ($K_d$) for the reversible binding between said binding site Z and said partner C is in the range of $10^{-2}$ M to $10^{-13}$ M.

* * * * *